US011898011B2

(12) United States Patent
Diev et al.

(10) Patent No.: US 11,898,011 B2
(45) Date of Patent: Feb. 13, 2024

(54) POLYMERS FOR USE IN ELECTRONIC DEVICES

(71) Applicant: DUPONT ELECTRONICS, INC., Wilmington, DE (US)

(72) Inventors: Viacheslav V Diev, Wilmington, DE (US); Nora Sabina Radu, Landenberg, PA (US)

(73) Assignee: DUPONT ELECTRONICS, INC., Wilmington, DE (US)

( * ) Notice: Subject to any disclaimer, the term of this patent is extended or adjusted under 35 U.S.C. 154(b) by 349 days.

(21) Appl. No.: 17/169,926

(22) Filed: Feb. 8, 2021

(65) Prior Publication Data
US 2021/0261734 A1 Aug. 26, 2021

Related U.S. Application Data

(60) Provisional application No. 62/978,579, filed on Feb. 19, 2020.

(51) Int. Cl.
*C08G 73/10* (2006.01)
*C07D 221/14* (2006.01)
(Continued)

(52) U.S. Cl.
CPC ....... *C08G 73/1085* (2013.01); *C07D 221/14* (2013.01); *C07D 311/80* (2013.01); *C08G 69/00* (2013.01)

(58) Field of Classification Search
CPC ...... C08L 79/08; C08G 73/1078; C08G 73/10
See application file for complete search history.

(56) References Cited

U.S. PATENT DOCUMENTS 3,850,964 A 11/1974 Williams
5,166,308 A 11/1992 Kreuz et al.
5,298,331 A 3/1994 Kanakarajan et al.

FOREIGN PATENT DOCUMENTS

CN 1603354 11/2004
CN 102746511 4/2011
(Continued)

OTHER PUBLICATIONS

Chen et al Synthesis and Characterization of Sulfonated Block Copolyimides Derived from 4,4'-Sulfide-bis(naphthalic anhydride) for Proton Exchange Membranes, J. Appl. Polym. Sci. 2015, 132, 41501, published on Jan. 2015.*
(Continued)

*Primary Examiner* — Gregory Listvoyb

(57) ABSTRACT

Disclosed is a dianhydride having Formula I, and diamines having Formula IV and Formula VII

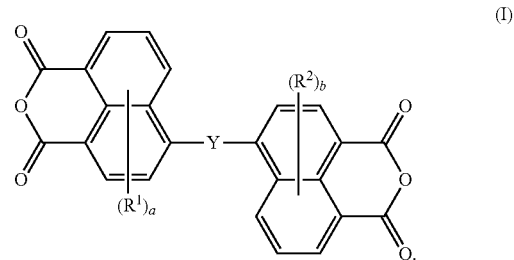

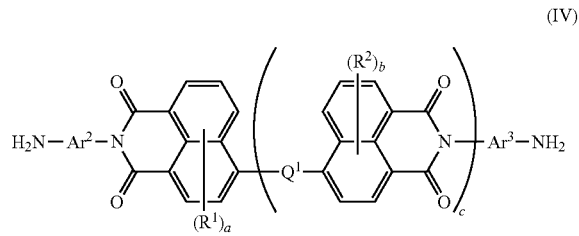

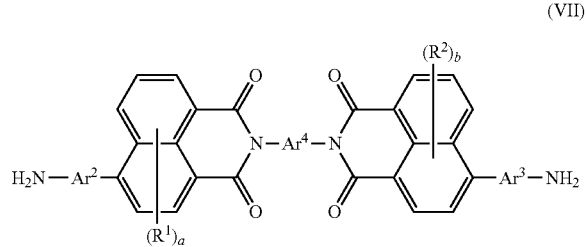

In the formulas: Y is alkyl, silyl, ester, siloxane, oligosiloxane, polysiloxane, O, S, $SO_2$, $BR^3$, $NR^3$, $P(O)R^3$, unsubstituted or substituted carbocyclic aryl, or unsubstituted or substituted heteroaryl and deuterated analogs thereof; $Ar^2$—$Ar^4$ are the same or different and are carbocyclic aryl, heteroaryl, or substituted derivatives thereof; $Q^1$ is a single bond, alkyl, silyl, ester, siloxane, oligosiloxane, polysiloxane, O, S, $SO_2$, $BR^3$, $NR^3$, $P(O)R^3$, unsubstituted or substituted carbocyclic aryl, or
unsubstituted or substituted heteroaryl and deuterated analogs thereof; $R^1$-$R^2$ are the same or different at each occurrence and are F, CN, deuterium, alkyl, fluoroalkyl, unsubstituted or substituted carbocyclic aryl, unsubstituted or substituted heteroaryl, alkoxy, fluoroalkoxy, unsubstituted or substituted aryloxy, silyl, siloxy and deuterated analogs thereof; $R^3$ is alkyl or unsubstituted or substituted carbocyclic aryl; a and b are the same or different and are an integer from 0-5; and c is 0 or 1.

10 Claims, 2 Drawing Sheets

(51) Int. Cl.
*C07D 311/80* (2006.01)
*C08G 69/00* (2006.01)

(56) References Cited

FOREIGN PATENT DOCUMENTS

| | | | |
|---|---|---|---|
| CN | 103951824 | | 3/2014 |
| CN | 107722271 | * | 2/2018 |
| JP | 2007-126610 | | 11/2005 |
| PL | 163253 | | 11/1990 |
| SU | 977457 A1 | | 1/1980 |

OTHER PUBLICATIONS

USPTO structure search, Apr. 2023.*
CRC Handbook of Chemistry and Physics, 81st Edition (2000-2001) (no copy provided).
Ll et al., Polymer Degradation and Stability (2012), 97(9), 1581-1588.
Wang et al., "Synthesis and Properties of Polyimides from 4,4'-Binaphthyl-1,1',8,8'-tetracarboxylic Dianhydride," Journal of Polymer Science Part A: Polymer Chemistry, vol. 33, 1627-1635 (1995).

* cited by examiner

POLYMERS FOR USE IN ELECTRONIC DEVICES

CLAIM OF BENEFIT OF PRIOR APPLICATION

This application claims the benefit of U.S. Provisional Application No. 62/978,579, filed Feb. 19, 2020, which is incorporated in its entirety herein by reference.

BACKGROUND INFORMATION

Field of the Disclosure

The present disclosure relates to novel polymeric compounds. The disclosure further relates to methods for preparing such polymeric compounds and electronic devices having at least one layer comprising these materials.

Description of the Related Art

Materials for use in electronics applications often have strict requirements in terms of their structural, optical, thermal, electronic, and other properties. As the number of commercial electronics applications continues to increase, the breadth and specificity of requisite properties demand the innovation of materials with new and/or improved properties. Polyimides represent a class of polymeric compounds that has been widely used in a variety of electronics applications. They can serve as a flexible replacement for glass in electronic display devices provided that they have suitable properties. These materials can function as a component of Liquid Crystal Displays ("LCDs"), where their modest consumption of electrical power, light weight, and layer flatness are critical properties for effective utility. Other uses in electronic display devices that place such parameters at a premium include device substrates, substrates for color filter sheets, cover films, touch screen panels, and others.

A number of these components are also important in the construction and operation of organic electronic devices having an organic light emitting diode ("OLED"). OLEDs are promising for many display applications because of their high power conversion efficiency and applicability to a wide range of end-uses. They are increasingly being used in cell phones, tablet devices, handheld/laptop computers, and other commercial products. These applications call for displays with high information content, full color, and fast video rate response time in addition to low power consumption.

Polyimide films generally possess sufficient thermal stability, high glass transition temperature, and mechanical toughness to merit consideration for such uses. Also, polyimides generally do not develop haze when subject to repeated flexing, so they are often preferred over other transparent substrates like polyethylene terephthalate (PET) and polyethylene naphthalate (PEN) in flexible display applications. There is thus a continuing need for polymer materials that are suitable for use in electronic devices.

SUMMARY

Finding novel rigid structures that can lead to low CTE, high Tg, high thermal stability polymers remains challenging. Due to their low reactivity, uses of 1,8-naphthalic dianhydride and imide-containing polymers have been overlooked in literature despite significant recent interest in various aromatic compounds.

Herein are disclosed monomers that can be used for the fabrication of low CTE, high Tg, high thermal stability polyimide films.

Disclosed diimide-containing naphthalic monomers are reactive to form high molecular weight polymers at ambient conditions.

Furthermore, the monomers can be used in small amounts as additives to improve the color of polyimide films.

There is provided a dianhydride having Formula I

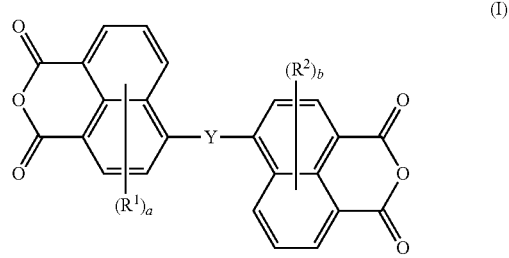

wherein:

Y is selected from the group consisting of alkyl, silyl, ester, siloxane, oligosiloxane, polysiloxane, O, S, $SO_2$, $BR^3$, $NR^3$, $P(O)R^3$, unsubstituted or substituted carbocyclic aryl, and unsubstituted or substituted heteroaryl;

$R^1$-$R^2$ are the same or different at each occurrence and are selected from the group consisting of F, CN, deuterium, alkyl, fluoroalkyl, unsubstituted or substituted carbocyclic aryl, unsubstituted or substituted heteroaryl, alkoxy, fluoroalkoxy, unsubstituted or substituted aryloxy, silyl, and siloxy, and deuterated analogs thereof;

$R^3$ is selected from the group consisting of alkyl and unsubstituted or substituted carbocyclic aryl and deuterated analogs thereof; and a and b are the same or different and are an integer from 0-5.

There is further provided a polyamic acid having a repeat unit of Formula II

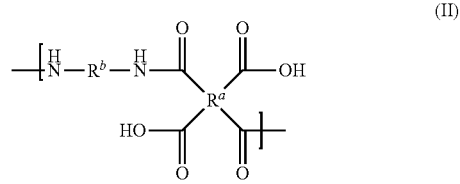

where:

$R^a$ is the same or different at each occurrence and represents one or more tetracarboxylic acid component residues; and $R^b$ is the same or different at each occurrence and represents one or more aromatic diamineresidues;

wherein 0.001-100 mol % of $R^a$ is a dianhydride residue from one or more dianhydrides having Formula I.

There is further provided a composition comprising (a) the polyamic acid having a repeat unit of Formula II and (b) a high-boiling, aprotic solvent.

There is further provided a polyimide whose repeat units have the structure in Formula III

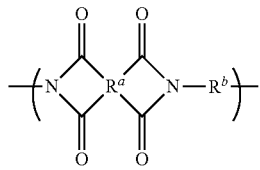
(III)

where $R^a$ and $R^b$ are as defined in Formula II.

There is further provided a polyimide film comprising the repeat unit of Formula III.

There is further provided a diamine having Formula IV

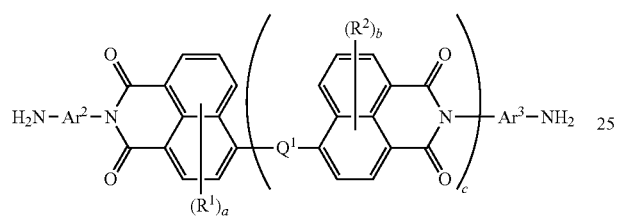
(IV)

wherein:
$Ar^2$ and $Ar^3$ are the same or different and are selected from the group consisting of carbocyclic aryl, heteroaryl, and substituted derivatives thereof;
$Q^1$ is selected from the group consisting of a single bond, alkyl, silyl, ester, siloxane, oligosiloxane, polysiloxane, O, S, $SO_2$, $BR^3$, $NR^3$, $P(O)R^3$, unsubstituted or substituted carbocyclic aryl, and unsubstituted or substituted heteroaryl;
$R^1$ and $R^2$ are the same or different at each occurrence and are selected from the group consisting of F, CN, deuterium, alkyl, fluoroalkyl, unsubstituted or substituted carbocyclic aryl, unsubstituted or substituted heteroaryl, alkoxy, fluoroalkoxy, unsubstituted or substituted aryloxy, silyl, and siloxy, and deuterated analogs thereof,
$R^3$ is selected from the group consisting of alkyl and unsubstituted or substituted carbocyclic aryl; and
a and b are the same or different and are an integer from 0-5; and c is 0 or 1.

There is further provided a polyamic acid having a repeat unit of Formula V

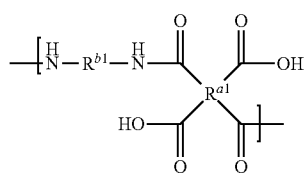
(V)

where:
$R^{a1}$ is the same or different at each occurrence and represents one or more tetracarboxylic acid component residues; and $R^{b1}$ is the same or different at each occurrence and represents one or more aromatic diamineresidues;
wherein 0.001-100 mol % of $R^{b1}$ is a diamine residue from one or more diamines having Formula IV.

There is further provided a composition comprising (a) the polyamic acid having a repeat unit of Formula V and (b) a high-boiling, aprotic solvent.

There is further provided a polyimide whose repeat units have the structure in Formula VI

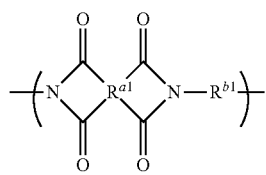
(VI)

where $R^{a1}$ and $R^{b1}$ are as defined in Formula IV.

There is further provided a diamine having Formula VII

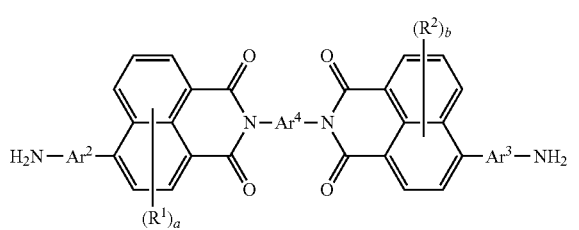
(VII)

wherein:
$Ar^2$, $Ar^3$, and $Ar^4$ are the same or different and are selected from the group consisting of carbocyclic aryl, heteroaryl, and substituted derivatives thereof;
$R^1$ and $R^2$ are the same or different at each occurrence and are selected from the group consisting of F, CN, deuterium, alkyl, fluoroalkyl, unsubstituted or substituted carbocyclic aryl, unsubstituted or substituted heteroaryl, alkoxy, fluoroalkoxy, unsubstituted or substituted aryloxy, silyl, and siloxy, and deuterated analogs thereof; and
a and b are the same or different and are an integer from 0-5.

There is further provided a polyamic acid having a repeat unit of Formula VIII

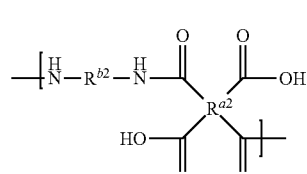
(VIII)

where:
$R^{a2}$ is the same or different at each occurrence and represents one or more tetracarboxylic acid component residues; and
$R^{b2}$ is the same or different at each occurrence and represents one or more aromatic diamineresidues;

wherein 0.001-100 mol % of $R^{b2}$ is a diamine residue from one or more diamines having Formula VII.

There is further provided a composition comprising (a) the polyamic acid having a repeat unit of Formula VIII and (b) a high-boiling, aprotic solvent.

There is further provided a polyimide whose repeat units have the structure in Formula IX

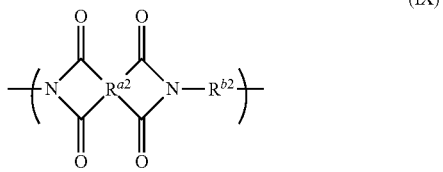

(IX)

where $R^{a2}$ and $R^{b2}$ are as defined in Formula VIII.

There is further provided a polyimide film comprising the repeat unit of Formula III, Formula VI, or Formula IX.

There is further provided one or more methods for preparing a polyimide film wherein the polyimide film has the repeat unit of Formula III, Formula VI, or Formula IX.

There is further provided a flexible replacement for glass in an electronic device wherein the flexible replacement for glass is a polyimide film having the repeat unit of Formula III, Formula VI, or Formula IX.

There is further provided an electronic device having at least one layer comprising a polyimide film having the repeat unit of Formula III, Formula VI, or Formula IX.

There is further provided an organic electronic device, such as an OLED, wherein the organic electronic device contains a flexible replacement for glass as disclosed herein.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
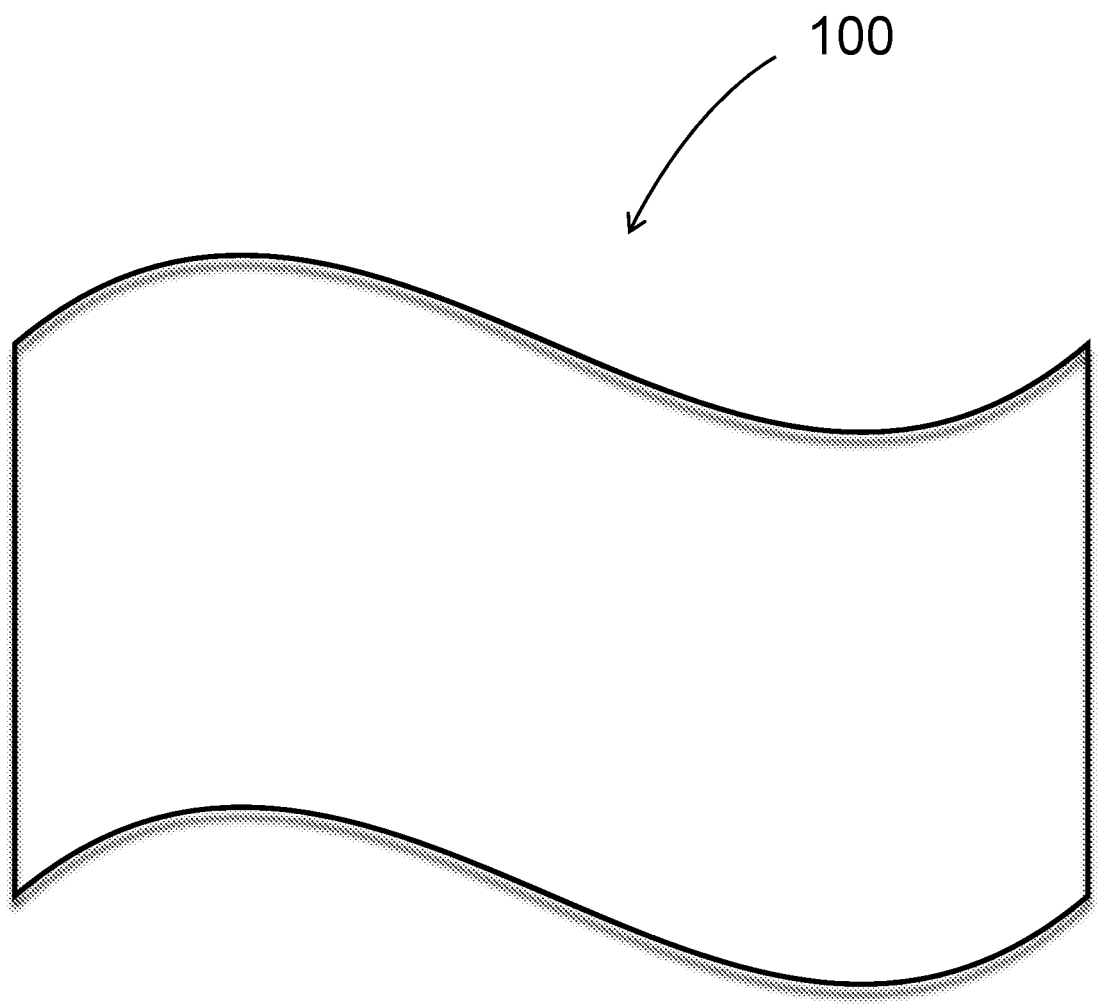
FIG. 1 includes an illustration of one example of a polyimide film that can be used as a flexible replacement for glass.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms, followed by the Dianhydride, the Diamine, the Polyamic Acid, the Polyimide, the Methods for Preparing the Polyimide Films, the Electronic Device, and finally Examples.

1. Definitions and Clarification of Terms

Before addressing details of embodiments described below, some terms are defined or clarified.

As used in the "Definitions and Clarification of Terms", R, $R^a$, $R^b$, R', R" and any other variables are generic designations and may be the same as or different from those defined in the formulas.

The term "alkyl" is intended to mean a group derived from an aliphatic hydrocarbon and includes a linear, a branched, or a cyclic group, which may be unsubstituted or substituted. In some embodiments, alkyl groups have 1 to 20 carbon atoms. In some embodiments, the group has 1 to 6 carbon atoms. A "heteroalkyl" group is an alkyl group in which at least one carbon the the chain has been replaced by a heteroatom. In some embodiments, the heteroalkyl group has 1 to 20 carbon atoms.

The term "aprotic" refers to a class of solvents that lack an acidic hydrogen atom and are therefore incapable of acting as hydrogen donors. Common aprotic solvents include alkanes, carbon tetrachloride (CCl4), benzene, dimethyl formamide (DMF), N-methyl-2-Pyrrolidone (NMP), dimethylacetamide (DMAc), and many others.

The term "aromatic compound" is intended to mean an organic compound comprising at least one unsaturated cyclic group having 4n+2 delocalized pi electrons. The term is intended to encompass both aromatic compounds having only carbon and hydrogen atoms, and heteroaromatic compounds wherein one or more of the carbon atoms within the cyclic group has been replaced by another atom, such as nitrogen, oxygen, sulfur, or the like.

The term "aryl" or "aryl group" a moiety formed by removal of one or more hydrogen ("H") or deuterium ("D") from an aromatic compound. The aryl group may be a single ring (monocyclic) or have multiple rings (bicyclic, or more) fused together or linked covalently. A "carbocyclic aryl" has only carbon atoms in the aromatic ring(s). A "heteroaryl" has one or more heteroatoms in at least one aromatic ring. In some embodiments, carbocyclicaryl groups have 6 to 60 ring carbon atoms; in some embodiments, 6 to 30 ring carbon atoms. In some embodiments, heteroaryl groups have from 4-50 ring carbon atoms; in some embodiments, 4-30 ring carbon atoms.

The term "alkoxy" is intended to mean the group —OR, where R is alkyl.

The term "aryloxy" is intended to mean the group —OR, where R is aryl.

Unless otherwise indicated, all groups can be substituted or unsubstituted. An optionally substituted group, such as, but not limited to, alkyl or aryl, may be substituted with one or more substituents which may be the same or different. Suitable substituents include alkyl, aryl, nitro, cyano, —N(R')(R"), halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, silyl, siloxy, siloxane, thioalkoxy, —S(O)$_2$—, —C(=O)—N(R')(R"), (R')(R")N-alkyl, (R')(R")N-alkoxyalkyl, (R')(R")N-alkylaryloxyalkyl, —S(O)$_s$-aryl (where s=0–2) or —S(O)$_s$-heteroaryl (where s=0–2).

The term "amine" is intended to mean a compound that contains a basic nitrogen atom with a lone pair. The term "amino" refers to the functional group —NH$_2$, —NHR, or —NR$_2$, where R is the same or different at each occurrence and can be an alkyl group or an aryl group. The term "diamine" is intended to mean a compound that contains two basic nitrogen atoms with associated lone pairs. The term "aromatic diamine" is intended to mean an aromatic compound having two amino groups. The term "bent diamine" is intended to mean a diamine wherein the two basic nitrogen atoms and associated lone pairs are asymmetrically disposed about the center of symmetry of the corresponding compound or functional group, e.g. m-phenylenediamine:

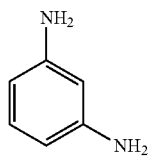

The term "aromatic diamine residue" is intended to mean the moiety bonded to the two amino groups in an aromatic diamine. The term "aromatic diisocyanate residue" is intended to mean the moiety bonded to the two isocyanate groups in an aromatic diisocyanate compound. This is further illustrated below.

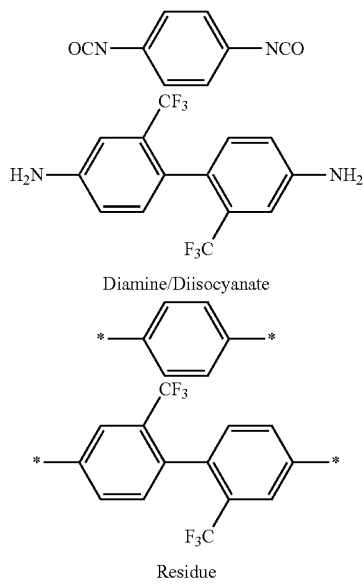

The terms "diamine residue" and "diisocyanate residue" are intended to mean the moiety bonded to two amino groups or two isocyanate groups, respectively, where the moiety is aliphatic or aromatic.

The term "b*" is intended to mean the b* axis in the CIELab Color Space that represents the yellow/blue opponent colors. Yellow is represented by positive b* values, and blue is represented by negative b* values. Measured b* values may be affected by solvent, particularly since solvent choice may affect color measured on materials exposed to high-temperature processing conditions. This may arise as the result of inherent properties of the solvent and/or properties associated with low levels of impurities contained in various solvents. Particular solvents are often preselected to achieve desired b* values for a particular application.

The term "birefringence" is intended to mean the difference in the refractive index in different directions in a polymer film or coating. This term usually refers to the difference between the x- or y-axis (in-plane) and the z-axis (out-of-plane) refractive indices.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "compound" is intended to mean an electrically uncharged substance made up of molecules that further include atoms, wherein the atoms cannot be separated from their corresponding molecules by physical means without breaking chemical bonds. The term is intended to include oligomers and polymers.

The term "linear coefficient of thermal expansion (CTE or α)" is intended to mean the parameter that defines the amount which a material expands or contracts as a function of temperature. It is expressed as the change in length per degree Celsius and is generally expressed in units of μm/m/° C. or ppm/° C.

$$\alpha = (\Delta L/L_0)/\Delta T$$

Measured CTE values disclosed herein are made via known methods during the first or second heating scan. The understanding of the relative expansion/contraction characteristics of materials can be an important consideration in the fabrication and/or reliability of electronic devices.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "electroactive" as it refers to a layer or a material, is intended to indicate a layer or material which electronically facilitates the operation of the device. Examples of electroactive materials include, but are not limited to, materials which conduct, inject, transport, or block a charge, where the charge can be either an electron or a hole, or materials which emit radiation or exhibit a change in concentration of electron-hole pairs when receiving radiation. Examples of inactive materials include, but are not limited to, planarization materials, insulating materials, and environmental barrier materials.

The term "tensile elongation" or "tensile strain" is intended to mean the percentage increase in length that occurs in a material before it breaks under an applied tensile stress. It can be measured, for example, by ASTM Method D882.

The prefix "fluoro" is intended to indicate that one or more hydrogens in a group have been replaced with fluorine.

The term "glass transition temperature (or $T_g$)" is intended to mean the temperature at which a reversible change occurs in an amorphous polymer or in amorphous regions of a semi crystalline polymer where the material changes suddenly from a hard, glassy, or brittle state to one that is flexible or elastomeric. Microscopically, the glass transition occurs when normally-coiled, motionless polymer chains become free to rotate and can move past each other.

$T_g$'s may be measured using differential scanning calorimetry (DSC), thermo-mechanical analysis (TMA), or dynamic-mechanical analysis (DMA), or other methods.

The prefix "hetero" indicates that one or more carbon atoms have been replaced with a different atom. In some embodiments, the heteroatom is O, N, S, or combinations thereof.

The term "high-boiling" is intended to indicate a boiling point greater than 130° C.

The term "host material" is intended to mean a material to which a dopant is added. The host material may or may not have electronic characteristic(s) or the ability to emit, receive, or filter radiation. In some embodiments, the host material is present in higher concentration.

The term "laser particle counter test" refers to a method used to assess the particle content of polyamic acid and other polymeric solutions whereby a representative sample of a test solution is spin coated onto a 5" silicon wafer and soft baked/dried. The film thus prepared is evaluated for particle content by any number of standard measurement techniques. Such techniques include laser particle detection and others known in the art.

The term "liquid composition" is intended to mean a liquid medium in which a material is dissolved to form a solution, a liquid medium in which a material is dispersed to form a dispersion, or a liquid medium in which a material is suspended to form a suspension or an emulsion.

The term "matrix" is intended to mean a foundation on which one or more layers is deposited in the formation of, for example, an electronic device. Non-limiting examples include glass, silicon, and others.

The term "1% TGA Weight Loss" is intended to mean the temperature at which 1% of the original polymer weight is lost due to decomposition (excluding absorbed water).

The term "optical retardation (or $R_{TH}$)" is intended to mean the difference between the average in-plane refractive index and the out-of-plane refractive index (i.e., the birefringence), this difference then being multiplied by the thickness of the film or coating. Optical retardation is typically measured for a given frequency of light, and the units are reported in nanometers.

The term "organic electronic device" or sometimes "electronic device" is herein intended to mean a device including one or more organic semiconductor layers or materials.

The term "particle content" is intended to mean the number or count of insoluble particles that is present in a solution. Measurements of particle content can be made on the solutions themselves or on finished materials (pieces, films, etc.) prepared from those films. A variety of optical methods can be used to assess this property.

The term "photoactive" refers to a material or layer that emits light when activated by an applied voltage (such as in a light emitting diode or chemical cell), that emits light after the absorption of photons (such as in down-converting phosphor devices), or that responds to radiant energy and generates a signal with or without an applied bias voltage (such as in a photodetector or a photovoltaic cell).

The term "polyamic acid solution" refers to a solution of a polymer containing amic acid units that have the capability of intramolecular cyclization to form imide groups.

The term "polyimide" refers to condensation polymers resulting from the reaction of one or more bifunctional carboxylic acid components with one or more primary diamines or diisocyanates. They contain the imide structure —CO—NR—CO— as a linear or heterocyclic unit along the main chain of the polymer backbone.

The term "satisfactory," when regarding a materials property or characteristic, is intended to mean that the property or characteristic fulfills all requirements/demands for the material in-use.

The term "soft-baking" is intended to mean a process commonly used in electronics manufacture wherein coated materials are heated to drive off solvents and solidify a film. Soft-baking is commonly performed on a hot plate or in exhausted oven at temperatures between 90° C. and 110° C. as a preparation step for subsequent thermal treatment of coated layers or films.

The term "substrate" refers to a base material that can be either rigid or flexible and may include one or more layers of one or more materials, which can include, but are not limited to, glass, polymer, metal or ceramic materials or combinations thereof. The substrate may or may not include electronic components, circuits, or conductive members.

The term "siloxane" refers to the group $R_3SiOR_2Si$— or the bivalent group —$SiR_2OR_2Si$—, where R is the same or different at each occurrence and is H, C1-20 alkyl, fluoroalkyl, or aryl. In some embodiments, one or more carbons in an R alkyl group are replaced with Si. An oligomeric siloxane has 2-5 repeating siloxane units. A polymeric siloxane has more than 5 repeating siloxane units; in some embodiments, 6-12 repeating siloxane units.

The term "siloxy" refers to the group $R_3SiO$—, where R is the same or different at each occurrence and is H, C1-20 alkyl, fluoroalkyl, or aryl.

The term "silyl" refers to the group $R(R_2Si)_n$—, or the bivalent group —$(R_2Si)_n$—, where R is the same or different at each occurrence and is H, C1-20 alkyl, fluoroalkyl, or aryl. In some embodiments, one or more carbons in an R alkyl group are replaced with Si. In some embodiments, n is 1-10.

The term "spin coating" is intended to mean a process used to deposit uniform thin films onto flat substrates. Generally, a small amount of coating material is applied on the center of the substrate, which is either spinning at low speed or not spinning at all. The substrate is then rotated at specified speeds in order to spread the coating material uniformly by centrifugal force.

The term "tensile modulus" is intended to mean the measure of the stiffness of a solid material that defines the initial relationship between the stress (force per unit area) and the strain (proportional deformation) in a material like a film. Commonly used units are gigapascals (GPa).

The term "tetracarboxylic acid component" is intended to mean any one or more of the following: a tetracarboxylic acid, a tetracarboxylic acid monoanhydride, a tetracarboxylic acid dianhydride, a tetracarboxylic acid monoester, and a tetracarboxylic acid diester.

The term "tetracarboxylic acid component residue" is intended to mean the moiety bonded to the four carboxy groups in a tetracarboxylic acid component. This is further illustrated below.

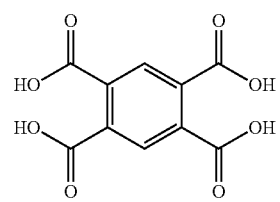

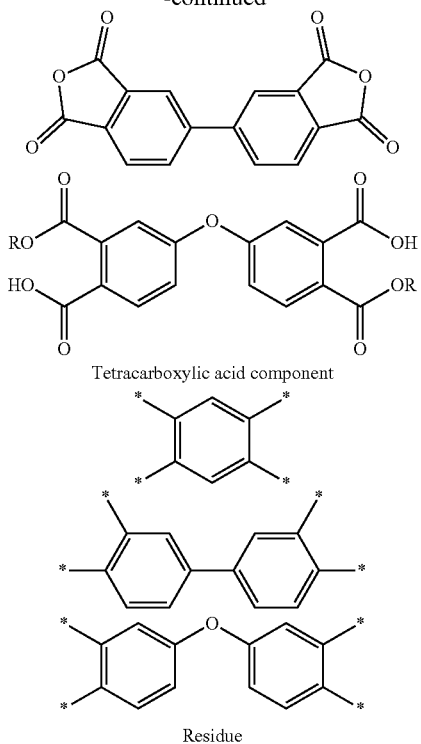

Tetracarboxylic acid component

Residue

The term "transmittance" refers to the percentage of light of a given wavelength impinging on a film that passes through the film so as to be detectable on the other side. Light transmittance measurements in the visible region (380 nm to 800 nm) are particularly useful for characterizing film-color characteristics that are most important for understanding the properties-in-use of the polyimide films disclosed herein.

The term "yellowness index (or YI)" refers to the magnitude of yellowness relative to a standard. A positive value of YI indicates the presence, and magnitude, of a yellow color. Materials with a negative YI appear bluish. It should also be noted, particularly for polymerization and/or curing processes run at high temperatures, that YI can be solvent dependent. The magnitude of color introduced using DMAC as a solvent, for example, may be different than that introduced using NMP as a solvent. This may arise as the result of inherent properties of the solvent and/or properties associated with low levels of impurities contained in various solvents. Particular solvents are often preselected to achieve desired YI values for a particular application.

In a structure where a substituent bond passes through one or more rings as shown below,

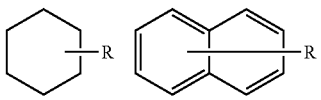

it is meant that the substituent R may be bonded at any available position on the one or more rings.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). Exemplary adjacent R groups are shown below:

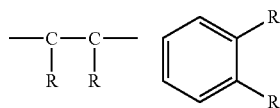

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the CRC Handbook of Chemistry and Physics, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Dianhydride

The dianhydride described herein has Formula I

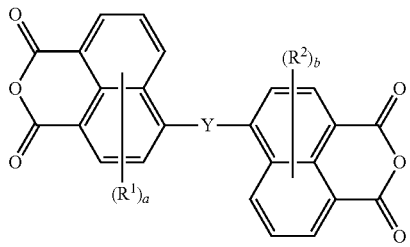

wherein:
- Y is selected from the group consisting of alkyl, silyl, ester, siloxane, oligosiloxane, polysiloxane, O, S, $SO_2$, $BR^3$, $NR^3$, $P(O)R^3$, unsubstituted or substituted carbocyclic aryl, and unsubstituted or substituted heteroaryl, and deuterated analogs thereof;
- $R^1$-$R^2$ are the same or different at each occurrence and are selected from the group consisting of F, CN, deuterium, alkyl, fluoroalkyl, unsubstituted or substituted carbocyclic aryl, unsubstituted or substituted heteroaryl, alkoxy, fluoroalkoxy, unsubstituted or substituted aryloxy, silyl, and siloxy, and deuterated analogs thereof;
- $R^3$ is selected from the group consisting of alkyl and unsubstituted or substituted carbocyclic aryl and deuterated analogs thereof; and
- a and b are the same or different and are an integer from 0-5.

In some embodiments of Formula I, Y is a $C_{1-6}$ alkyl; in some embodiments, a $C_{4-6}$ cycloalkyl. In some embodiments, the alkyl is further substituted with one or more substituents selected from the group consisting of F, CN, deuterium, alkyl, fluoroalkyl, unsubstituted or substituted carbocyclic aryl, unsubstituted or substituted heteroaryl, alkoxy, fluoroalkoxy, unsubstituted or substituted aryloxy, silyl, and siloxy and deuterated analogs thereof. In some embodiments, the one or more substituent is selected from the group consisting of F, CN, alkyl, fluoroalkyl, and fluoroalkoxy and deuterated analogs thereof.

In some embodiments of Formula I, Y is a $C_{2-6}$ silyl.
In some embodiments of Formula I, Y is an ester.
In some embodiments of Formula I, Y is siloxane.
In some embodiments of Formula I, Y is an oligosiloxane.
In some embodiments of Formula I, Y is a polysiloxane.
In some embodiments of Formula I, Y is O.
In some embodiments of Formula I, Y is S.
In some embodiments of Formula I, Y is $SO_2$.
In some embodiments of Formula I, Y is B.
In some embodiments of Formula I, Y is $NR^3$.
In some embodiments of Formula I, Y is $P(O)R^3$.
In some embodiments of Formula I, Y is an unsubstituted carbocyclic aryl having 6-20 ring carbon atoms; in some embodiments, 6-12 ring carbon atoms.
In some embodiments of Formula I, Y is a substituted carbocyclic aryl having 6-20 ring carbon atoms and having one or more substituent selected from the group consisting of F, CN, deuterium, alkyl, fluoroalkyl, alkoxy, fluoroalkoxy, silyl, and siloxy and deuterated analogs thereof. In some embodiments, the carbocyclic aryl is selected from the group consisting of phenyl, biphenyl, naphthyl, binaphthyl, and anthracenyl.

In some embodiments of Formula I, Y is an unsubstituted heteroaryl having 6-18 ring carbon atoms and at least one ring heteroatom selected from the group consisting of N, O, and S.

In some embodiments of Formula I, Y is a substituted heteroaryl having 6-18 ring carbon atoms and having one or more substituent selected from the group consisting of F, CN, alkyl, fluoroalkyl, alkoxy, fluoroalkoxy, silyl, and siloxy.

In some embodiments of Formula I, the heteroaryl group is derived from a compound selected from the group consisting of pyridine, carbazole, dibenzofuran, and dibenzothiophene.

In some embodiments of Formula I, a=0.
In some embodiments of Formula I, a=1.
In some embodiments of Formula I, a=2.
In some embodiments of Formula I, a=3.
In some embodiments of Formula I, a=4.
In some embodiments of Formula I, a=5.
In some embodiments of Formula I, a>0.
In some embodiments of Formula I, a>0 and at least one $R^1$ is F.
In some embodiments of Formula I, a>0 and at least one $R^1$ is CN.
In some embodiments of Formula I, a>0 and at least one $R^1$ is a $C_{1-20}$ alkyl; in some embodiments $C_{1-10}$ alkyl.
In some embodiments of Formula I, a>0 and at least one $R^1$ is a $C_{1-20}$ fluoroalkyl; in some embodiments $C_{1-10}$ fluoroalkyl.
In some embodiments of Formula I, a>0 and at least one $R^1$ is a $C_{1-20}$ perfluorofluoroalkyl; in some embodiments $C_{1-10}$ perfluoroalkyl.
In some embodiments of Formula I, a>0 and at least one $R^1$ is a $C_{1-20}$ alkoxy; in some embodiments $C_{1-10}$ alkoxy.
In some embodiments of Formula I, a>0 and at least one $R^1$ is a $C_{1-20}$ fluoroalkoxy; in some embodiments $C_{1-10}$ fluoroalkoxy.
In some embodiments of Formula I, a>0 and at least one $R^1$ is a $C_{1-20}$ perfluoroalkoxy; in some embodiments $C_{1-10}$ perfluoroalkoxy.
In some embodiments of Formula I, a>0 and at least one $R^1$ is $SiH_3$.
In some embodiments of Formula I, a>0 and at least one $R^1$ is a $C_{1-12}$ silyl; in some embodiments $C_{3-6}$ silyl.
In some embodiments of Formula I, a>0 and at least one $R^1$ is a $C_{1-12}$ siloxy; in some embodiments $C_{3-6}$ siloxy.
In some embodiments of Formula I, a>0 and at least one $R^1$ is an unsubstituted or substituted $C_{6-30}$ hydrocarbon aryl; in some embodiments, an unsubstituted or substituted $C_{6-18}$ hydrocarbon aryl; in some embodiments, unsubstituted.
In some embodiments of Formula I, a>0 and at least one $R^1$ is an unsubstituted or substituted $C_{3-30}$ heteroaryl; in some embodiments, an unsubstituted or substituted $C_{3-18}$ heteroaryl; in some embodiments, unsubstituted.
In some embodiments of Formula I, a>0 and at least one $R^1$ is an unsubstituted or substituted $C_{6-30}$ hydrocarbon aryloxy; in some embodiments, an unsubstituted or substituted $C_{6-18}$ hydrocarbon aryloxy; in some embodiments, unsubstituted.
In some embodiments, any of the above hydrocarbon aryl, heteroaryl, and aryloxy groups are further substituted with one or more substituents selected from the group consisting of F, CN, alkyl, fluoroalkyl, alkoxy, fluoroalkoxy, silyl, and siloxy.
In some embodiments of Formula I, a=1 and $R^1$ is selected from the group consisting of F, trifluoromethyl, and trifluoromethoxy.

All of the above-described embodiments for a in Formula I, apply equally to b in Formula I.

In some embodiments, b>0 and all of the above-described embodiments for $R^1$ apply equally to $R^2$.

In some embodiments of Formula I, b=1 and $R^2$ is selected from the group consisting of F, trifluoromethyl, and trifluoromethoxy.

In some embodiments of Formula I, $R^3$ is a $C_{1-20}$ alkyl; in some embodiments $C_{1-10}$ alkyl.

In some embodiments of Formula I, $R^3$ is an unsubstituted carbocyclic aryl having 6-20 ring carbon atoms; in some embodiments, 6-12 ring carbon atoms.

In some embodiments of Formula I, $R^3$ is a substituted carbocyclic aryl having 6-20 ring carbon atoms and having one or more substituent selected from the group consisting of F, CN, alkyl, fluoroalkyl, alkoxy, fluoroalkoxy, silyl, and siloxy.

In some embodiments of Formula I, the dianhydride has Formula IA

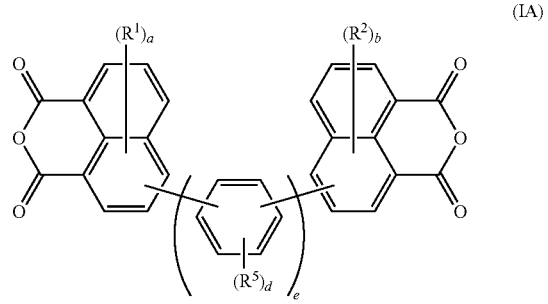

(IA)

wherein:
  $R^5$ is the same or different at each occurrence and is the same or different at each occurrence and are selected from the group consisting of F, CN, deuterium, alkyl, fluoroalkyl, unsubstituted or substituted carbocyclic aryl, unsubstituted or substituted heteroaryl, alkoxy, fluoroalkoxy, unsubstituted or substituted aryloxy, silyl, and siloxy and deuterated analogs thereof;
  d is an integer from 0-4;
  e is an integer from 1-5; and
  $R^1$, $R^2$, a, and b are as defined in Formula I.

In some embodiments of Formula IA, d=0.
In some embodiments of Formula IA, d=1.
In some embodiments of Formula IA, d=2.
In some embodiments of Formula IA, d=3.
In some embodiments of Formula IA, d=4.
In some embodiments of Formula IA, d>0.
In some embodiments of Formula IA, e=1.
In some embodiments of Formula IA, e=2.
In some embodiments of Formula IA, e=3.
In some embodiments of Formula IA, e=4.
In some embodiments of Formula IA, e=5.

In some embodiments of Formula IA, d>0 and all the above-described embodiments for $R^1$ in Formula I apply equally to $R^5$ in Formula IA.

All of the above-described embodiments for $R^1$, $R^2$, a, and b in Formula I, apply equally to $R^1$, $R^2$, a, and b in Formula I.

The new compounds can be made using any technique that will yield a C—C or C—N bond, or other desired bond. A variety of such techniques are known, such as Suzuki, Yamamoto, Stille, Negishi, and metal-catalyzed C—N couplings as well as metal catalyzed and oxidative direct arylation. One synthetic scheme is shown below:

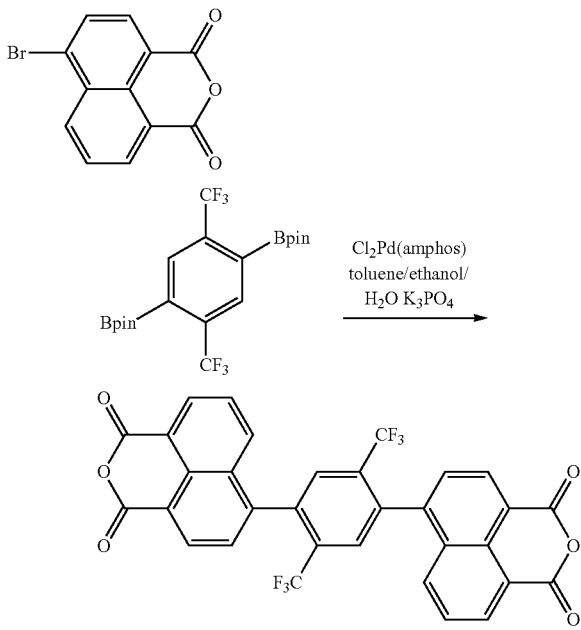

Any of the above embodiments for Formula I can be combined with one or more of the other embodiments, so long as they are not mutually exclusive. For example, the embodiment in which the dianhydride has Formula IA can be combined with the embodiment in which a=1 and $R^1$ is $CF_3$, and with the embodiment in which b=1 and $R^2$ is $CF_3$. The skilled person would understand which embodiments were mutually exclusive and would thus readily be able to determine the combinations of embodiments that are contemplated by the present application.

Some non-limiting examples of compounds having Formula I are shown below.

Compound I-1

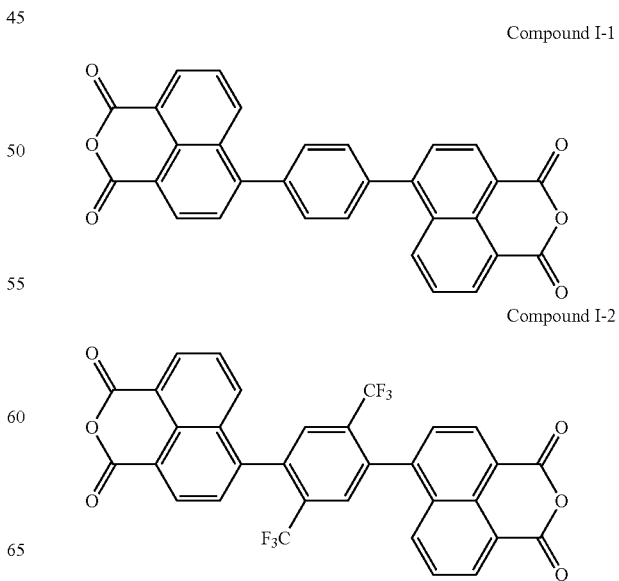

Compound I-2

Compound I-3

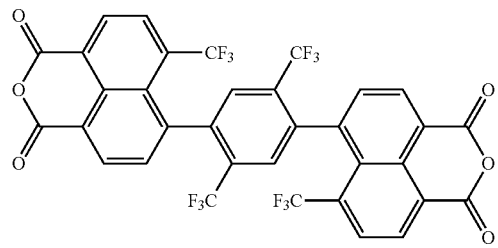

Compound I-4

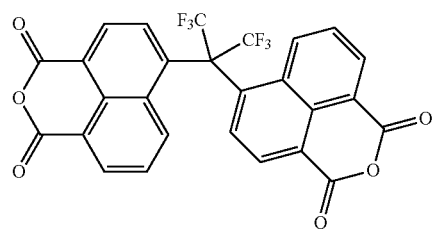

Compound I-5

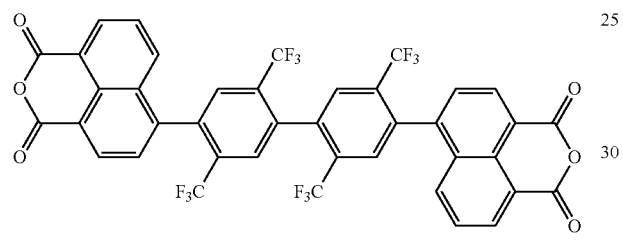

Compound I-6

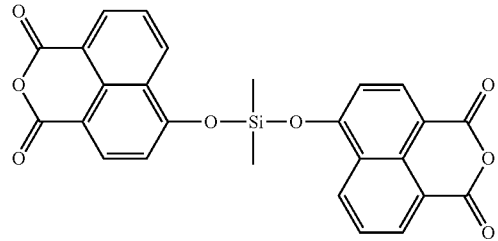

Compound I-7

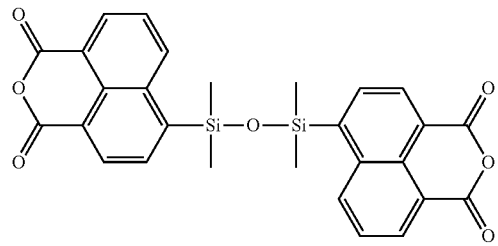

Compound I-8

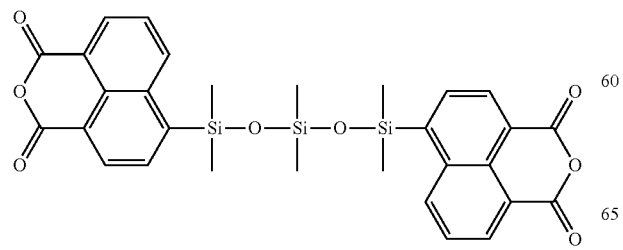

Compound I-9

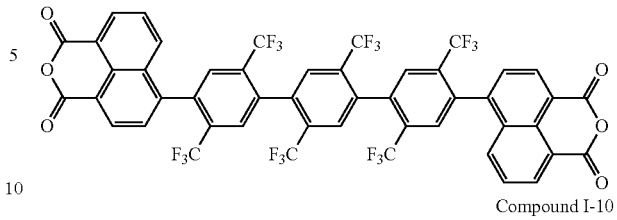

Compound I-10

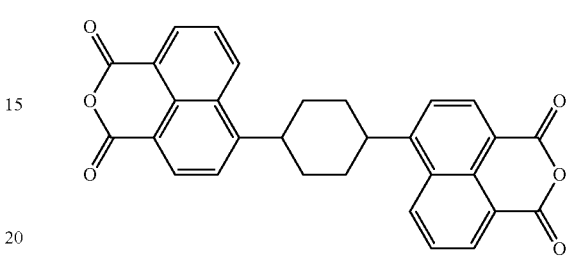

3. Diamines

The diamines described herein have Formula IV or Formula VII

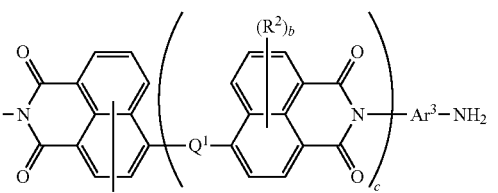

(IV)

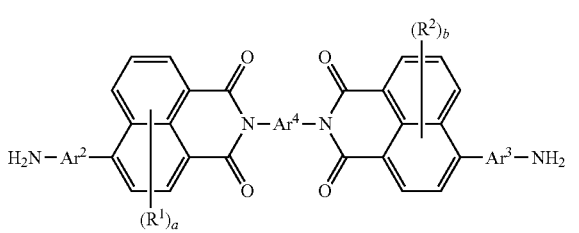

(VII)

wherein:
- $Ar^2$, $Ar^3$, and $Ar^4$ are the same or different and are selected from the group consisting of carbocyclic aryl, heteroaryl, substituted derivatives thereof and their deuterated analogs
- $Q^1$ is selected from the group consisting of a single bond, alkyl, silyl, ester, siloxane, oligosiloxane, polysiloxane, S, $SO_2$, B, $NR^3$, $P(O)R^3$, unsubstituted or substituted carbocyclic aryl, unsubstituted or substituted heteroaryl and deuterated analogs thereof;
- $R^1$ and $R^2$ are the same or different at each occurrence and are selected from the group consisting of F, CN, deuterium, alkyl, fluoroalkyl, unsubstituted or substituted carbocyclic aryl, unsubstituted or substituted heteroaryl, alkoxy, fluoroalkoxy, unsubstituted or substituted aryloxy, silyl, and siloxy and deuterated analogs thereof;

R³ is selected from the group consisting of alkyl and unsubstituted or substituted carbocyclic aryl; and a and b are the same or different and are an integer from 0-5; and c is 0 or 1.

In some embodiments, the diamine has Formula IV.

In some embodiments of Formula IV, c=0.

In some embodiments of Formula IV, c=1 and Q¹ is a single bond.

In some embodiments of Formula IV, c=1 and Q¹ is a $C_{1-6}$ alkyl; in some embodiments, a $C_{4-6}$ cycloalkyl. In some embodiments, the alkyl is further substituted with one or more substituents selected from the group consisting of F, CN, deuterium, alkyl, fluoroalkyl, unsubstituted or substituted carbocyclic aryl, unsubstituted or substituted heteroaryl, alkoxy, fluoroalkoxy, unsubstituted or substituted aryloxy, silyl, siloxy and deuterated analogs thereof. In some embodiments, the one or more substituent is selected from the group consisting of F, CN, alkyl, fluoroalkyl, and fluoroalkoxy.

In some embodiments of Formula IV, c=1 and Q¹ is a $C_{2-6}$ silyl.

In some embodiments of Formula IV, c=1 and Q¹ is an ester.

In some embodiments of Formula IV, c=1 and Q¹ is siloxane.

In some embodiments of Formula IV, c=1 and Q¹ is an oligosiloxane.

In some embodiments of Formula IV, c=1 and Q¹ is a polysiloxane.

In some embodiments of Formula IV, c=1 and Q¹ is O.

In some embodiments of Formula IV, c=1 and Q¹ is S.

In some embodiments of Formula IV, c=1 and Q¹ is $SO_2$.

In some embodiments of Formula IV, c=1 and Q¹ is B.

In some embodiments of Formula IV, c=1 and Q¹ is NR³.

In some embodiments of Formula IV, c=1 and Q¹ is P(O)R³.

In some embodiments of Formula IV, c=1 and Q¹ is an unsubstituted carbocyclic aryl having 6-20 ring carbon atoms; in some embodiments, 6-12 ring carbon atoms.

In some embodiments of Formula IV, c=1 and Q¹ is is a substituted carbocyclic aryl having 6-20 ring carbon atoms and having one or more substituent selected from the group consisting of F, CN, alkyl, fluoroalkyl, alkoxy, fluoroalkoxy, silyl, and siloxy.

In some embodiments, the carbocyclic aryl is selected from the group consisting of phenyl, biphenyl, naphthyl, binaphthyl, and anthracenyl.

In some embodiments of Formula IV, c=1 and Q¹ is an unsubstituted heteroaryl having 6-18 ring carbon atoms and at least one ring heteroatom selected from the group consisting of N, O, and S.

In some embodiments of Formula IV, c=1 and Q¹ is a substituted heteroaryl having 6-18 ring carbon atoms and having one or more substituent selected from the group consisting of F, CN, alkyl, fluoroalkyl, alkoxy, fluoroalkoxy, silyl, and siloxy.

In some embodiments, the heteroaryl group is derived from a compound selected from the group consisting of pyridine, carbazole, dibenzofuran, and dibenzothiophene.

In some embodiments of Formula IV, Ar² is an unsubstituted carbocyclic aryl having 6-20 ring carbon atoms; in some embodiments, 6-12 ring carbon atoms.

In some embodiments of Formula IV, Ar² is is a substituted carbocyclic aryl having 6-20 ring carbon atoms and having one or more substituent selected from the group consisting of F, CN, alkyl, fluoroalkyl, alkoxy, fluoroalkoxy, silyl, and siloxy.

In some embodiments, the carbocyclic aryl is selected from the group consisting of phenyl, biphenyl, naphthyl, binaphthyl, and anthracenyl.

In some embodiments of Formula IV, Ar² is an unsubstituted heteroaryl having 6-18 ring carbon atoms and at least one ring heteroatom selected from the group consisting of N, O, and S.

In some embodiments of Formula IV, Ar² is a substituted heteroaryl having 6-18 ring carbon atoms and having one or more substituent selected from the group consisting of F, CN, alkyl, fluoroalkyl, alkoxy, fluoroalkoxy, silyl, and siloxy.

In some embodiments, the heteroaryl group is derived from a compound selected from the group consisting of pyridine, carbazole, dibenzofuran, and dibenzothiophene.

All of the above-described embodiments for Ar² in Formula IV, apply equally to Ar³ in Formula IV.

All of the above-described embodiments for R¹, R², R³, a, and b in Formula I, apply equally to R¹, R², R³, a, and b in Formula IV.

In some embodiments of Formula IV, the diamine has Formula IVA, Formula IVB, or Formula IVC

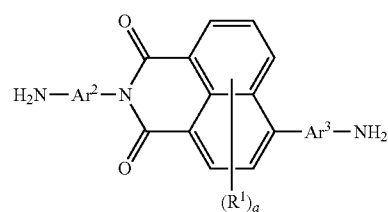

(IVA)

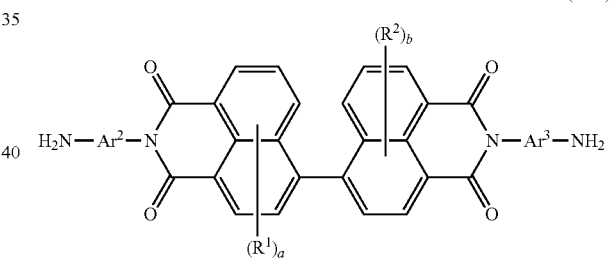

(IVB)

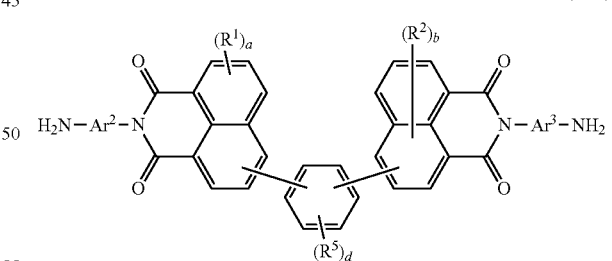

(IVC)

wherein:
R⁵ is the same or different at each occurrence and is the same or different at each occurrence and are selected from the group consisting of F, CN, deuterium, alkyl, fluoroalkyl, unsubstituted or substituted carbocyclic aryl, unsubstituted or substituted heteroaryl, alkoxy, fluoroalkoxy, unsubstituted or substituted aryloxy, silyl, siloxy and deuterated analogs thereof;
d is an integer from 0-4; and
Ar², Ar³, R¹, R², a, and b are as defined in Formula IV.

In some embodiments of Formula IVC, d=0.

In some embodiments of Formula IVC, d=1.
In some embodiments of Formula IVC, d=2.
In some embodiments of Formula IVC, d=3.
In some embodiments of Formula IVC, d=4.
In some embodiments of Formula IVC, d>0.
In some embodiments of Formula IVC, d>0 and all the above-described embodiments for $R^1$ in Formula I apply equally to $R^5$ in Formula IVC.

All of the above-described embodiments for $Ar^2$, $Ar^3$, $R^1$, $R^2$, a, and b in Formula IV, apply equally to $Ar^2$, $Ar^3$, $R^1$, $R^2$, a, and b in Formula IVA, Formula IVB, and Formula IVC.

In some embodiments, the diamine has Formula VII.

In some embodiments of Formula VII, $Ar^4$ is an unsubstituted carbocyclic aryl having 6-20 ring carbon atoms; in some embodiments, 6-12 ring carbon atoms.

In some embodiments of Formula VII, $Ar^4$ is a substituted carbocyclic aryl having 6-20 ring carbon atoms and having one or more substituent selected from the group consisting of F, CN, alkyl, fluoroalkyl, alkoxy, fluoroalkoxy, silyl, and siloxy.

In some embodiments, the carbocyclic aryl is selected from the group consisting of phenyl, biphenyl, naphthyl, binaphthyl, and anthracenyl.

In some embodiments of Formula VII, $Ar^4$ is an unsubstituted heteroaryl having 6-18 ring carbon atoms and at least one ring heteroatom selected from the group consisting of N, O, and S.

In some embodiments of Formula VII, $Ar^4$ is a substituted heteroaryl having 6-18 ring carbon atoms and having one or more substituent selected from the group consisting of F, CN, alkyl, fluoroalkyl, alkoxy, fluoroalkoxy, silyl, and siloxy.

In some embodiments of Formula VII, the heteroaryl group is derived from a compound selected from the group consisting of pyridine, carbazole, dibenzofuran, and dibenzothiophene.

All of the above-described embodiments for $Ar^2$, $Ar^3$, $R^1$, $R^2$, a, and b in Formula IV, apply equally to $Ar^2$, $Ar^3$, $R^1$, $R^2$, a, and b in Formula VII.

The new compounds can be made using any technique that will yield a C—C or C—N bond, or other desired bond. A variety of such techniques are known, such as Suzuki, Yamamoto, Stille, Negishi, and metal-catalyzed C—N couplings as well as metal catalyzed and oxidative direct arylation. Two synthetic schemes are shown below.

Formula IV

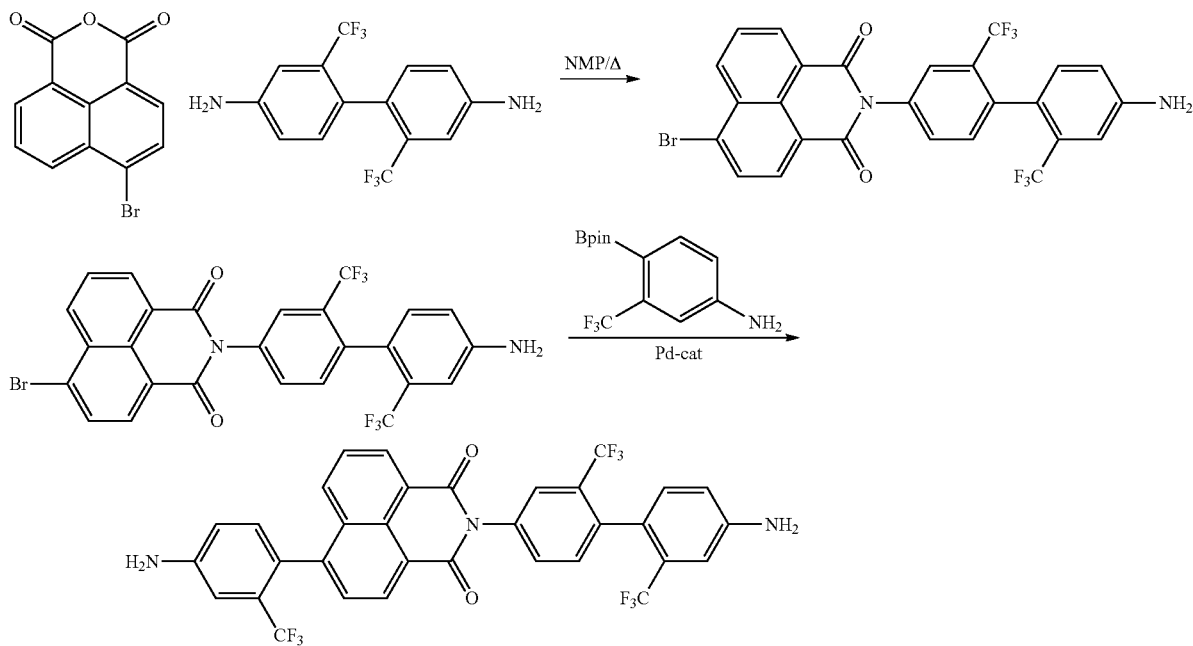

Formula VII

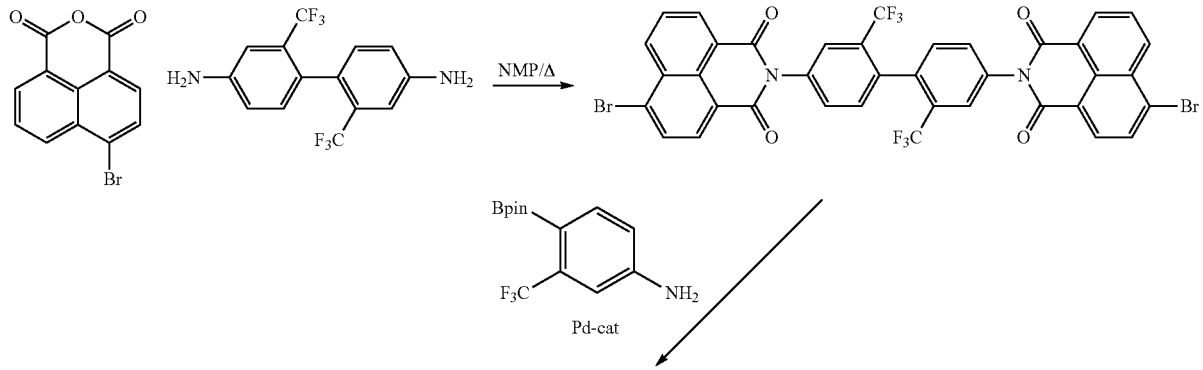

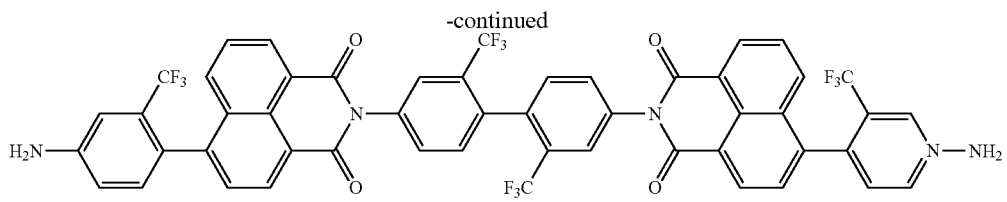

Any of the above embodiments for Formula IV can be combined with one or more of the other embodiments, so long as they are not mutually exclusive. For example, the embodiment in which the diamine has Formula IVB can be combined with the embodiment in which a=1 and $R^1$ is $CF_3$, and with the embodiment in which b=1 and $R^2$ is $CF_3$. The skilled person would understand which embodiments were mutually exclusive and would thus readily be able to determine the combinations of embodiments that are contemplated by the present application.

Any of the above embodiments for Formula VII can be combined with one or more of the other embodiments, so long as they are not mutually exclusive. For example, the embodiment in which $Ar^4$ is phenyl can be combined with the embodiment in which a=b=0. The skilled person would understand which embodiments were mutually exclusive and would thus readily be able to determine the combinations of embodiments that are contemplated by the present application.

Some non-limiting examples of compounds having Formula IV are shown below.

-continued
Compound IV-5
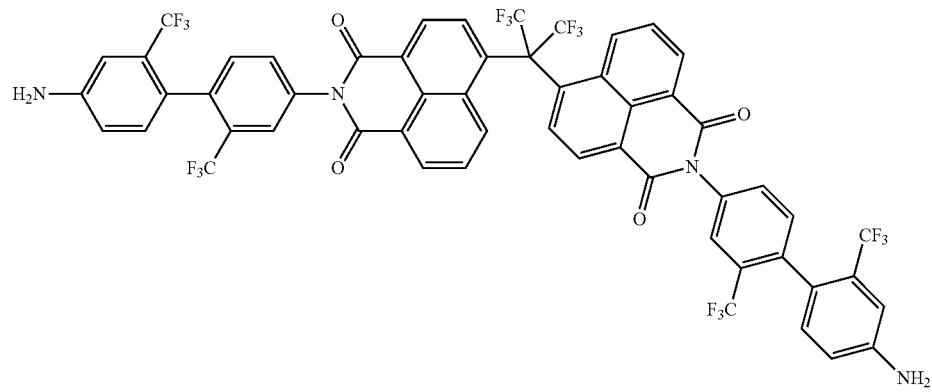
Compound IV-6
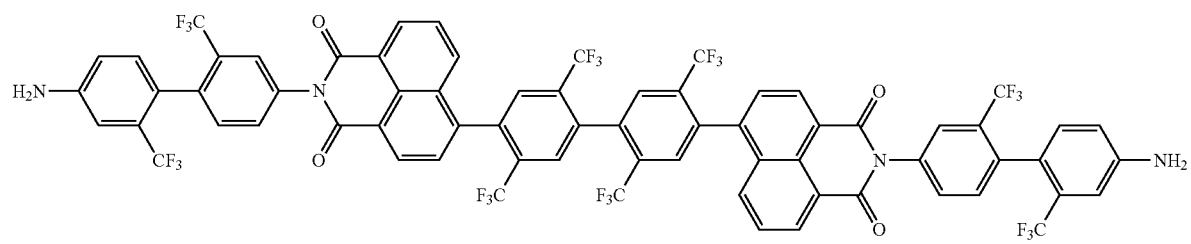
Compound IV-7
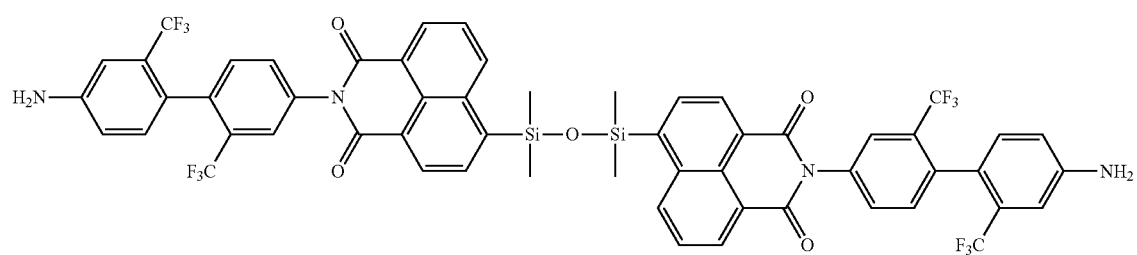
Compound IV-8
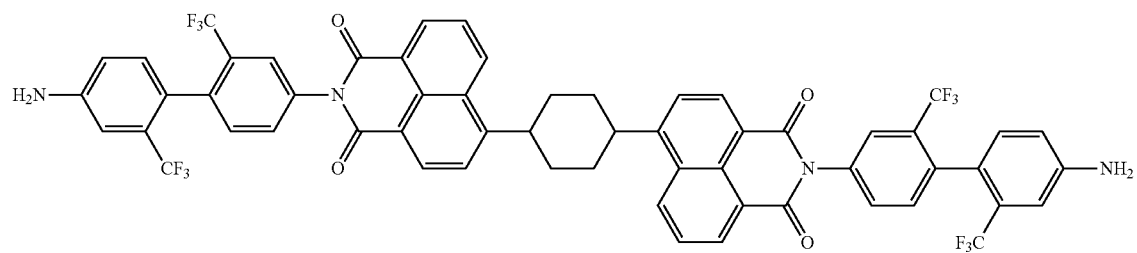
Compound IV-9
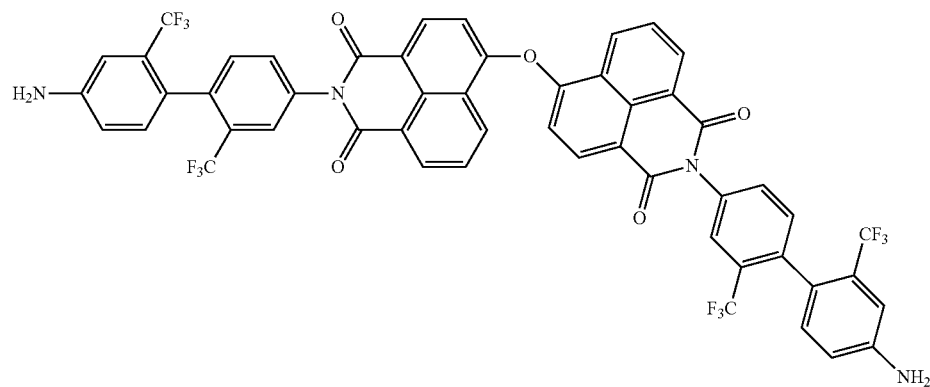

Some non-limiting examples of compounds having Formula VII are shown below.

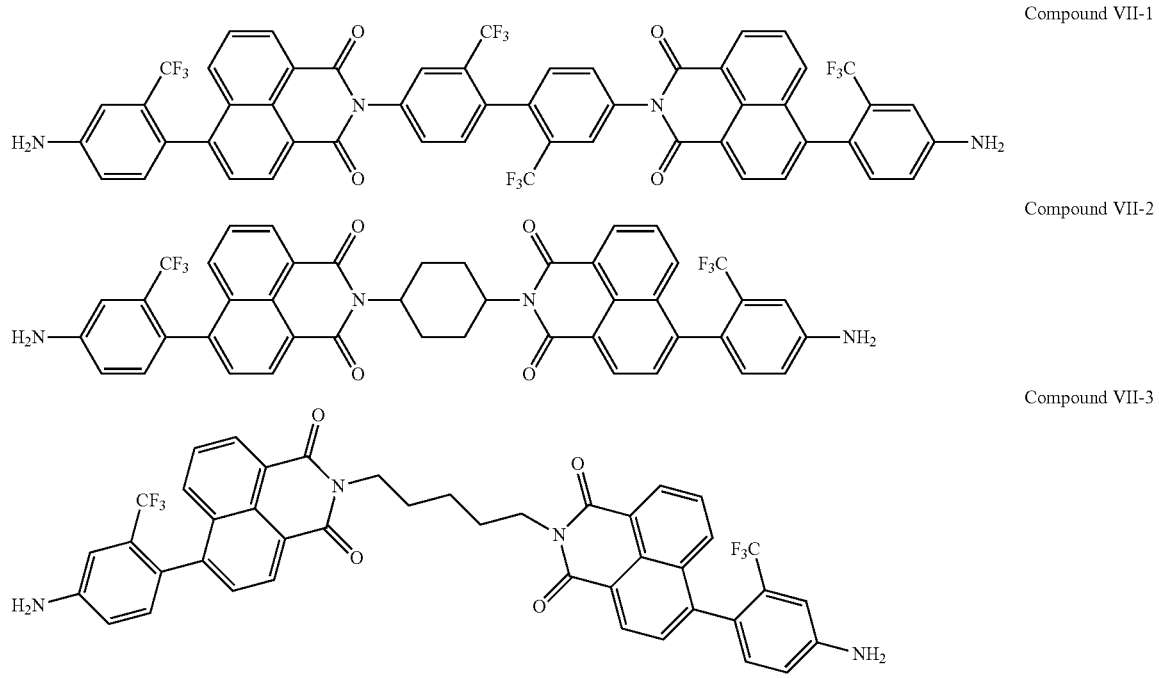

Compound VII-1

Compound VII-2

Compound VII-3

4. Polyamic Acids

In some embodiments, the polyamic acid has a repeat unit structure of Formula II

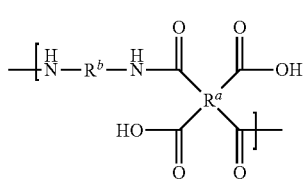

(II)

where:
- $R^a$ is the same or different at each occurrence and represents one or more tetracarboxylic acid component residues; and
- $R^b$ is the same or different at each occurrence and represents one or more aromatic diamine residues;

wherein 0.001-100 mol % of $R^a$ is a residue from one or more dianhydrides having Formula I.

In some embodiments of Formula II, the residue of the dianhydride having Formula I is present as an additive to improve the color of the polyamic acid and the polyimide film formed from the polyamic acid. The dianhydride having Formula I can lower the apparent color so that the film appears less yellow.

In some embodiments of Formula II, the dianhydride having Formula I is present as an additive, and 0.001-10 mol % of $R^a$ is a residue from one or more dianhydrides having Formula I; in some embodiments, 0.01-5 mol %; in some embodiments 0.1-1.0 mol %. In some embodiments, a single dianhydride having Formula I is used as an additive.

In some embodiments of Formula II, the dianhydride having Formula I is present in order to improve properties such as CTE, Tg, and thermal stability of polyimide films made from the polyamic acid.

In some embodiments of Formula II, the dianhydride having Formula I is present to improve the properties of the final polyimide film and 10-100 mol % of $R^a$ is a residue from one or more dianhydrides having Formula I; in some embodiments, 20-100 mol %; in some embodiments, 30-100 mol %; in some embodiments, 40-100 mol %; in some embodiments, 50-100 mol %; in some embodiments, 60-100 mol %; in some embodiments, 70-100 mol %; in some embodiments, 80-100 mol %; in some embodiments, 90-100 mol %; in some embodiments, 100 mol %.

In some embodiments of Formula II, 10-100 mol % of $R^a$ represents a dianhydride residue from one dianhydride having Formula I, as shown above.

In some embodiments of Formula II, 10-100 mol % of $R^a$ represents a dianhydride residue from two different dianhydrides which both have Formula I, as shown above.

In some embodiments of Formula II, 10-100 mol % of $R^a$ represents a dianhydride residue from three different dianhydrides which all have Formula I, as shown above.

In some embodiments of Formula II, 10-100 mol % of $R^a$ represents a dianhydride residue from four or more different dianhydrides which all have Formula I, as shown above.

In some embodiments of Formula II, 10-90 mol % of $R^a$ is a residue from one or more dianhydrides having Formula I; in some embodiments, 20-80 mol %; in some embodiments, 30-70 mol %.

Any of the above embodiments for Formula I in Formula II can be combined with one or more of the other embodiments, so long as they are not mutually exclusive.

In some embodiments of Formula II, $R^a$ represents a dianhydride residue from one or more dianhydrides having Formula I and at least one additional dianhydride residue.

In some embodiments of Formula II, $R^a$ represents a dianhydride residue from one or more dianhydrides having Formula I and one additional dianhydride residue.

In some embodiments of Formula II, $R^a$ represent a dianhydride residue from one or more dianhydrides having Formula I and two additional dianhydride residues.

In some embodiments of Formula II, $R^a$ represents a dianhydride residue from one or more dianhydrides having Formula I and three additional dianhydride residues.

In some embodiments, the additional dianhydride residue is the residue from a dianhydride selected from the group consisting of pyromellitic dianhydride (PMDA), 3,3',4,4'-biphenyl tetracarboxylic dianhydride (BPDA), 4,4'-oxydiphthalic anhydride(ODPA), 4,4'-hexafluoroiso-propylidenebisphthalic dianhydride (6FDA), 3,3',4,4'-benzophenone tetracarboxylic dianhydride (BTDA), bis(1,3-dioxo-1,3-dihydroisobenzofuran-5-carboxylic acid) 1,4-phenylene ester (TAHQ), 3,3',4,4'-diphenylsulfone tetracarboxylic dianhydride (DSDA), 4,4'-bisphenol-A dianhydride (BPADA), hydroquinone diphthalic anhydride (HQ-DEA), ethylene glycol bis(trimellitic anhydride) (TMEG-100), 4-(2,5-dioxotetrahydrofuran-3-yl)-1,2,3,4-tetrahydronapthalene-1,2-dicarboyxlic anhydride (DTDA); 4,4'-bisphenol A dianhydride (BPADA), and the like, combinations thereof and deuterated analogs thereof. These aromatic dianhydrides may optionally be substituted with groups that are known in the art including deuterium, alkyl, aryl, nitro, cyano, —N(R')(R"), halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, silyl, siloxy, siloxane, thioalkoxy, —S(O)$_2$—, —C(=O)—N(R')(R"), (R')(R")N-alkyl, (R')(R")N-alkoxyalkyl, (R')(R")N-alkylaryloxyalkyl, —S(O)$_s$-aryl (where s=0–2) or —S(O)$_s$-heteroaryl (where s=0–2) and deuterated analogs thereof. Each R' and R" is independently an optionally substituted alkyl, cycloalkyl, or aryl group. R' and R", together with the nitrogen atom to which they are bound, can form a ring system in certain embodiments. Substituents may also be crosslinking groups.

In some embodiments of Formula II, the additional dianhydride residue is from one or more tetracarboxylic acid dianhydrides selected from the group consisting of PMDA, BPDA, 6FDA, and BTDA.

In some embodiments of Formula II, $R^b$ represents a single diamine residue.

In some embodiments of Formula II, $R^b$ represents two diamine residues.

In some embodiments of Formula II, $R^b$ represents three diamine residues.

In some embodiments of Formula II, $R^b$ representsfour diamine residues.

In some embodiments of Formula II, $R^b$ representsone or more diamine residues.

Examples of suitable aromatic diamines include, but are not limited to, p-phenylene diamine (PPD), 2,2'-dimethyl-4,4'-diaminobiphenyl (m-tolidine), 3,3'-dimethyl-4,4'-diaminobiphenyl (o-tolidine), 3,3'-dihydroxy-4,4'-diaminobiphenyl (HAB), 9,9'-bis(4-aminophenyl)fluorene (FDA), o-tolidine sulfone (TSN), 2,3,5,6-tetramethyl-1,4-phenylenediamine (TMPD), 2,4-diamino-1,3,5-trimethyl benzene (DAM), 3,3',5,5'-tetramethylbenzidine (3355TMB), 2,2'-bis(trifluoromethyl) benzidine (22TFMB or TFMB), 2,2-bis[4-(4-aminophenoxy)phenyl]propane (BAPP), 4,4'-methylene dianiline (MDA), 4,4'-[1,3-phenylenebis(1-methyl-ethylidene)]bisaniline (Bis-M), 4,4'-[1,4-phenylenebis(1-methyl-ethylidene)]bisaniline (Bis-P), 4,4'-oxydianiline (4,4'-ODA), m-phenylene diamine (MPD), 3,4'-oxydianiline (3,4'-ODA), 3,3'-diaminodiphenyl sulfone (3,3'-DDS), 4,4'-diaminodiphenyl sulfone (4,4'-DDS), 4,4'-diaminodiphenyl sulfide (ASD), 2,2-bis[4-(4-amino-phenoxy)phenyl]sulfone (BAPS), 2,2-bis[4-(3-aminophenoxy)-phenyl]sulfone (m-BAPS), 1,4'-bis(4-aminophenoxy)benzene (TPE-Q), 1,3'-bis(4-aminophenoxy)benzene (TPE-R), 1,3'-bis(4-amino-phenoxy)benzene (APB-133), 4,4'-bis(4-aminophenoxy)biphenyl (BAPB), 4,4'-diaminobenzanilide (DABA), methylene bis(anthranilic acid) (MBAA), 1,3'-bis(4-aminophenoxy)-2,2-dimethylpropane (DANPG), 1,5-bis(4-aminophenoxy)pentane (DA5MG), 2,2'-bis[4-(4-aminophenoxy pehnyl)]hexafluoropropane (HFBAPP), 2,2-bis(4-aminophenyl) hexafluoropropane (Bis-A-AF), 2,2-bis(3-amino-4-hydroxyphenyl) hexafluoropropane (Bis-AP-AF), 2,2-bis(3-amino-4-methylphenyl) hexafluoropropane (Bis-ΔT-AF), 4,4'-bis(4-amino-2-trifluoromethyl phenoxy)biphenyl (6BFBAPB), 3,3'5,5'-tetramethyl-4,4'-diamino diphenylmethane (TMMDA), and the like their combinations and deuterated analogs thereof.

In some embodiments of Formula II, $R^b$ represents a diamine residue from one or more diamines selected from the group consisting of PPD, 4,4'-ODA, 3,4'-ODA, TFMB, Bis-A-AF, Bis-ΔT-AF, and Bis-P.

In some embodiments, the polyamic acid has a repeat unit structure of Formula V

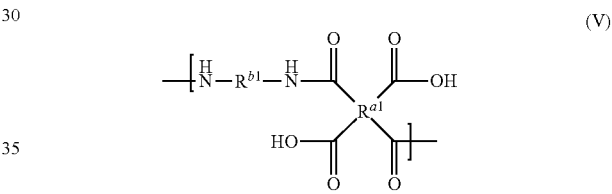

(V)

where:
$R^{a1}$ is the same or different at each occurrence and represents one or more tetracarboxylic acid component residues; and
$R^{b1}$ is the same or different at each occurrence and representsone or more aromatic diamineresidues;
wherein 0.001-100 mol % of $R^{b1}$ is a residue from one or more diamines having Formula IV.

In some embodiments of Formula V, $R^{a1}$ represents a single tetracarboxylic acid component residue.

In some embodiments of Formula V, $R^{a1}$ represents two tetracarboxylic acid component residues.

In some embodiments of Formula V, $R^{a1}$ represents three tetracarboxylic acid residues.

In some embodiments of Formula V, $R^{a1}$ representsfour tetracarboxylic acid residues.

In some embodiments of Formula V, $R^{a1}$ representsone or more tetracarboxylic acid dianhydride residues.

Examples of suitable aromatic tetracarboxylic acid dianhydrides include, but are not limited to, those given above with respect to Formula II.

In some embodiments of Formula V, $R^{a1}$ represents one or more residues from tetracarboxylic acid dianhydrides selected from the group consisting of PMDA, BPDA, 6FDA, and BTDA.

In some embodiments of Formula V, $R^{a1}$ represents a PMDA residue.

In some embodiments of Formula V, $R^{a1}$ represents a BPDA residue.

In some embodiments of Formula V, $R^{a1}$ represents a 6FDA residue.

In some embodiments of Formula V, $R^{a1}$ represents a BTDA residue.

In some embodiments of Formula V, $R^{a1}$ represents a PMDA residue and a BPDA residue.

In some embodiments of Formula V, $R^{a1}$ represents a PMDA residue and a 6FDA residue.

In some embodiments of Formula V, $R^{a1}$ represents a PMDA residue and a BTDA residue.

In some embodiments of Formula V, $R^{a1}$ represents a BPDA residue and a 6FDA residue.

In some embodiments of Formula V, $R^{a1}$ represents a BPDA residue and a BTDA residue.

In some embodiments of Formula V, $R^{a1}$ represents a 6FDA residue and a BTDA residue.

In some embodiments of Formula V, $R^{a1}$ represents a PMDA residue a BPDA residue, and a 6FDA residue.

In some embodiments of Formula V, the residue of the diamine having Formula IV is present as an additive to improve the color of the polyamic acid and the polyimide film formed from the polyamic acid. The diamine having Formula IV can lower the apparent color so that the film appears less yellow.

In some embodiments of Formula V, the diamine having Formula IV is present as an additive, and 0.001-10 mol % of $R^{b1}$ is a residue from one or more diamines having Formula IV; in some embodiments, 0.01-5 mol %; in some embodiments 0.1-1.0 mol %. In some embodiments, a single diamine having Formula IV is used as an additive.

In some embodiments of Formula V, the diamine having Formula IV is present in order to improve properties such as CTE, Tg, and thermal stability of polyimide films made from the polyamic acid.

In some embodiments of Formula V, the diamine having Formula IV is present to improve the properties of the final polyimide film and 10-100 mol % of $R^{b1}$ is a residue from one or more diamines having Formula IV; in some embodiments, 20-100 mol %; in some embodiments, 30-100 mol %; in some embodiments, 40-100 mol %; in some embodiments, 50-100 mol %; in some embodiments, 60-100 mol %; in some embodiments, 70-100 mol %; in some embodiments, 80-100 mol %; in some embodiments, 90-100 mol %; in some embodiments, 100 mol %.

In some embodiments of Formula V, 10-100 mol % of $R^{b1}$ represents a diamine residue from one diamine having Formula IV, as shown above.

In some embodiments of Formula V, 10-100 mol % of $R^{b1}$ represents a diamine residue from two different diamines which both have Formula IV, as shown above.

In some embodiments of Formula V, 10-100 mol % of $R^{b1}$ represents a diamine residue from three different diamines which all have Formula IV, as shown above.

In some embodiments of Formula V, 10-100 mol % of $R^{b1}$ represents a diamine residue from four or more different diamines which all have Formula IV, as shown above.

Any of the above embodiments for Formula IV in Formula V can be combined with one or more of the other embodiments, so long as they are not mutually exclusive.

In some embodiments of Formula V, $R^{b1}$ represents a diamine residue from one or more diamineshaving Formula IV and at least one additional diamine residue.

In some embodiments of Formula V, $R^{b1}$ represents a diamine residue from one or more diamines having Formula IV and one additional diamine residue.

In some embodiments of Formula V, $R^{b1}$ represents a diamine residue from one or more diamines having Formula IV and two additional diamine residues.

In some embodiments of Formula V, $R^{b1}$ represents a diamine residue from one or more diamines having Formula IV and three additional diamine residues.

Examples of suitable additional diamines include, but are not limited to, those given above with respect to Formula II.

In some embodiments of Formula V, $R^{b1}$ represents a diamine residue from one or more diamineshaving Formula IV and the diamine residue from at least one additional diamine, where the additional diamine is selected from the group consisting of PPD, 4,4'-ODA, 3,4'-ODA, TFMB, Bis-A-AF, Bis-ΔT-AF, and Bis-P.

In some embodiments, the polyamic acid has a repeat unit structure of Formula VII

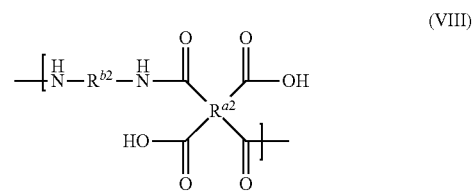

(VIII)

where:
$R^{a2}$ is the same or different at each occurrence and represents one or more tetracarboxylic acid component residues; and
$R^{b2}$ is the same or different at each occurrence and representsone or more aromatic diamineresidues;
wherein 0.001-100 mol % of $R^{b2}$ is a residue from one or more diamines having Formula VII.

All of the above-described embodiments for $R^{a1}$ in Formula V apply equally to $R^{a2}$ in Formula VIII.

In some embodiments of Formula VIII, the residue of the diamine having Formula VII is present as an additive to improve the color of the polyamic acid and the polyimide film formed from the polyamic acid. The diamine having Formula VII can lower the apparent color so that the film appears less yellow.

In some embodiments of Formula VIII, the diamine having Formula VII is present as an additive, and 0.001-10 mol % of $R^{b2}$ is a residue from one or more diamines having Formula VII; in some embodiments, 0.01-5 mol %; in some embodiments 0.1-1.0 mol %. In some embodiments, a single diamine having Formula VII is used as an additive.

In some embodiments of Formula VIII, the diamine having Formula VII is present in order to improve properties such as CTE, Tg, and thermal stability of polyimide films made from the polyamic acid.

In some embodiments of Formula VIII, the diamine having Formula VII is present to improve the properties of the final polyimide film and 10-100 mol % of $R^{b2}$ is a residue from one or more diamines having Formula VII; in some embodiments, 20-100 mol %; in some embodiments, 30-100 mol %; in some embodiments, 40-100 mol %; in some embodiments, 50-100 mol %; in some embodiments, 60-100 mol %; in some embodiments, 70-100 mol %; in some embodiments, 80-100 mol %; in some embodiments, 90-100 mol %; in some embodiments, 100 mol %.

In some embodiments of Formula VIII, 10-100 mol % of $R^{b2}$ represents a diamine residue from one diamine having Formula VII, as shown above.

In some embodiments of Formula VIII, 10-100 mol % of $R^{b2}$ represents a diamine residue from two different diamines which both have Formula VII, as shown above.

In some embodiments of Formula VIII, 10-100 mol % of $R^{b2}$ represents a diamine residue from three different diamines which all have Formula VII, as shown above.

In some embodiments of Formula VIII, 10-100 mol % of $R^{b2}$ represents a diamine residue from four or more different diamines which all have Formula VII, as shown above.

In some embodiments of Formula VIII, 20-100 mol % of $R^{b2}$ is a residue from one or more diamines having Formula VII; in some embodiments, 30-100 mol %; in some embodiments, 40-100 mol %; in some embodiments, 50-100 mol %; in some embodiments, 60-100 mol %; in some embodiments, 70-100 mol %; in some embodiments, 80-100 mol %; in some embodiments, 90-100 mol %; in some embodiments, 100%.

Any of the above embodiments for Formula VII in Formula VIII can be combined with one or more of the other embodiments, so long as they are not mutually exclusive.

In some embodiments of Formula VIII, $R^{b2}$ represents a diamine residue from one or more diamines having Formula VII and at least one additional diamine residue.

In some embodiments of Formula VIII, $R^{b2}$ represents a diamine residue from one or more diamines having Formula VII and one additional diamine residue.

In some embodiments of Formula VIII, $R^{b2}$ represent a diamine residue from one or more diamines having Formula VII and two additional diamine residues.

In some embodiments of Formula VIII, $R^{b2}$ represents a diamine residue from one or more diamines having Formula VII and three additional diamine residues.

Examples of suitable additional diamines include, but are not limited to, those given above with respect to Formula II.

In some embodiments of Formula VIII, $R^{b2}$ represents a diamine residue from one or more diamines having Formula VII and the diamine residue from at least one additional diamine, where the additional diamine is selected from the group consisting of PPD, 4,4'-ODA, 3,4'-ODA, TFMB, Bis-A-AF, Bis-ΔT-AF, and Bis-P.

In some embodiments of Formula II, Formula V, and Formula VIII, moieties resulting from monoanhydride monomers are present as end-capping groups.

In some embodiments, the monoanhydride monomers are selected from the group consisting of phthalic anhydrides and the like and derivatives thereof.

In some embodiments, the monoanhydrides are present at an amount up to 5 mol % of the total tetracarboxylic acid composition.

In some embodiments of Formula II, Formula V, and Formula VIII, moieties resulting from monoamine monomers are present as end-capping groups.

In some embodiments, the monoamine monomers are selected from the group consisting of aniline and the like and derivatives thereof.

In some embodiments, the monoamines are present at an amount up to 5 mol % of the total amine composition.

In some embodiments, the polyamic acid has a weight average molecular weight (Mw) greater than 100,000 based on gel permeation chromatography with polystyrene standards.

In some embodiments, the polyamic acid has a weight average molecular weight (Mw) greater than 150,000 based on gel permeation chromatography with polystyrene standards.

In some embodiments, the polyamic acid has a molecular weight (Mw) greater than 200,000 based on gel permeation chromatography with polystyrene standards.

In some embodiments, the polyamic acid has a weight average molecular weight (Mw) greater than 250,000 based on gel permeation chromatography with polystyrene standards.

In some embodiments, the polyamic acid has a weight average molecular weight (Mw) greater than 300,000 based on gel permeation chromatography with polystyrene standards.

In some embodiments, the polyamic acid has a weight average molecular weight (Mw) between 100,000 and 400,000 based on gel permeation chromatography with polystyrene standards.

In some embodiments, the polyamic acid has a weight average molecular weight (Mw) between 200,000 and 400,000 based on gel permeation chromatography with polystyrene standards.

In some embodiments, the polyamic acid has a weight average molecular weight (Mw) between 250,000 and 350,000 based on gel permeation chromatography with polystyrene standards.

In some embodiments, the polyamic acid has a weight average molecular weight (Mw) between 200,000 and 300,000 based on gel permeation chromatography with polystyrene standards.

Any of the above embodiments for the polyamic acid can be combined with one or more of the other embodiments, so long as they are not mutually exclusive.

Overallpolyamic acid compositions can be designated via the notation commonly used in the art. For example, a polyamic acid having a tetracarboxylic acid component that is 100% ODPA, and a diamine component that is 90 mol % Bis-P and 10 mol % TFMB, would be represented as:

ODPA//Bis-P/22TFMB100//90/10.

There is also provided a liquid composition comprising (a) the polyamic acid having a repeat unit of Formula II, and (b) a high-boiling aprotic solvent. The liquid composition is also referred to herein as the "polyamic acid solution".

There is also provided a liquid composition comprising (a) the polyamic acid having a repeat unit of Formula V, and (b) a high-boiling aprotic solvent.

There is also provided a liquid composition comprising (a) the polyamic acid having a repeat unit of Formula VIII, and (b) a high-boiling aprotic solvent.

In some embodiments, the high-boiling aprotic solvent has a boiling point of 150° C. or higher.

In some embodiments, the high-boiling aprotic solvent has a boiling point of 175° C. or higher.

In some embodiments, the high-boiling aprotic solvent has a boiling point of 200° C. or higher.

In some embodiments, the high-boiling aprotic solvent is a polar solvent. In some embodiments, the solvent has a dielectric constant greater than 20.

Some examples of high-boiling aprotic solvents include, but are not limited to, N-methyl-2-pyrrolidone (NMP), dimethyl acetamide (DMAc), dimethyl sulfoxide (DMSO), dimethyl formamide (DMF), γ-butyrolactone, dibutyl carbitol, butyl carbitol acetate, diethylene glycol monoethyl ether acetate, propylene glycol monomethyl ether acetate and the like, and combinations thereof.

In some embodiments of the liquid composition, the solvent is selected from the group consisting of NMP, DMAc, and DMF.

In some embodiments of the liquid composition, the solvent is NMP.

In some embodiments of the liquid composition, the solvent is DMAc.

In some embodiments of the liquid composition, the solvent is DMF.

In some embodiments of the liquid composition, the solvent is γ-butyrolactone.

In some embodiments of the liquid composition, the solvent is dibutyl carbitol.

In some embodiments of the liquid composition, the solvent is butyl carbitol acetate.

In some embodiments of the liquid composition, the solvent is diethylene glycol monoethyl ether acetate.

In some embodiments of the liquid composition, the solvent is propylene glycol monoethyl ether acetate.

In some embodiments, more than one of the high-boiling aprotic solvents identified above is used in the liquid composition.

In some embodiments, additional cosolvents are used in the liquid composition.

In some embodiments, the liquid composition is <1 weight % polyamic acid in >99 weight % high-boiling aprotic solvent.

In some embodiments, the liquid composition is 1-5 weight % polyamic acid in 95-99 weight % high-boiling aprotic solvent.

In some embodiments, the liquid composition is 5-10 weight % polyamic acid in 90-95 weight % high-boiling aprotic solvent.

In some embodiments, the liquid composition is 10-15 weight % polyamic acid in 85-90 weight % high-boiling aprotic solvent.

In some embodiments, the liquid composition is 15-20 weight % polyamic acid in 80-85 weight % high-boiling aprotic solvent.

In some embodiments, the liquid composition is 20-25 weight % polyamic acid in 75-80 weight % high-boiling aprotic solvent.

In some embodiments, the liquid composition is 25-30 weight % polyamic acid in 70-75 weight % high-boiling aprotic solvent.

In some embodiments, the liquid composition is 30-35 weight % polyamic acid in 65-70 weight % high-boiling aprotic solvent.

In some embodiments, the liquid composition is 35-40 weight % polyamic acid in 60-65 weight % high-boiling aproticsolvent.

In some embodiments, the liquid composition is 40-45 weight % polyamic acid in 55-60 weight % high-boiling aprotic solvent.

In some embodiments, the liquid composition is 45-50 weight % polyamic acid in 50-55 weight % high-boiling aprotic solvent.

In some embodiments, the liquid composition is 50 weight % polyamic acid in 50 weight % high-boiling aprotic solvent.

The polyamic acid solutions can optionally further contain any one of a number of additives. Such additives can be: antioxidants, heat stabilizers, adhesion promoters, coupling agents (e.g. silanes), inorganic fillers or various reinforcing agents so long as they don't adversely impact the desired polyimide properties.

The polyamic acid solutions can be prepared using a variety of available methodswith respect to the introduction of the components (i.e., the monomers and solvents). Some methods of producing a polyamic acid solution include:

(a) a method wherein the diamine components and dianhydride components are preliminarily mixed together and then the mixture is added in portions to a solvent while stirring.

(b) a method wherein a solvent is added to a stirring mixture of diamine and dianhydride components. (contrary to (a) above)

(c) a method wherein diamines are exclusively dissolved in a solvent and then dianhydrides are added thereto at such a ratio as allowing to control the reaction rate.

(d) a method wherein the dianhydride components are exclusively dissolved in a solvent and then amine components are added thereto at such a ratio to allow control of the reaction rate.

(e) a method wherein the diamine components and the dianhydride components are separately dissolved in solvents and then these solutions are mixed in a reactor.

(f) a method wherein the polyamic acid with excessive amine component and another polyamic acid with excessive dianhydride component are preliminarily formed and then reacted with each other in a reactor, particularly in such a way as to create a non-random or block copolymer.

(g) a method wherein a specific portion of the amine components and the dianhydride components are first reacted and then the residual diamine components are reacted, or vice versa.

(h) a method wherein the components are added in part or in whole in any order to either part or whole of the solvent, also where part or all of any component can be added as a solution in part or all of the solvent.

(i) a method of first reacting one of the dianhydride components with one of the diamine components giving a first polyamic acid. Then reacting the other dianhydride component with the other amine component to give a second polyamic acid. Then combining the polyamic acids in any one of a number of ways prior to film formation.

Generally speaking, a polyamic acid solution can be obtained from any one of the polyamic acid solution preparation methods disclosed above.

The polyamic acid solution can then be filtered one or more times in order to reduce the particle content. The polyimide film generated from such a filtered solution can show a reduced number of defects and thereby lead to superior performance in the electronics applications disclosed herein. An assessment of the filtration efficiency can be made by the laser particle counter test wherein a representative sample of the polyamic acid solution is cast onto a 5" silicon wafer. After soft baking/drying, the film is evaluated for particle content by any number of laser particle counting techniques on instruments that are commercially available and known in the art.

In some embodiments, the polyamic acid solution is prepared and filtered to yield a particle content of less than 40 particles as measured by the laser particle counter test.

In some embodiments, the polyamic acid solution is prepared and filtered to yield a particle content of less than 30 particles as measured by the laser particle counter test.

In some embodiments, the polyamic acid solution is prepared and filtered to yield a particle content of less than 20 particles as measured by the laser particle counter test.

In some embodiments, the polyamic acid solution is prepared and filtered to yield a particle content of less than 10 particles as measured by the laser particle counter test.

In some embodiments, the polyamic acid solution is prepared and filtered to yield particle content of between 2 particles and 8 particles as measured by the laser particle counter test.

In some embodiments, the polyamic acid solution is prepared and filtered to yield particle content of between 4 particles and 6 particles as measured by the laser particle counter test.

Exemplary preparations of polyamic acid solutions are given in the examples.

5. Polyimides

In some embodiments, the polyimide has a repeat unit structure of Formula III

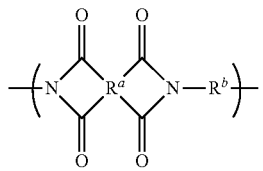

(III)

where
R$^a$ is the same or different at each occurrence and represents one or more tetracarboxylic acid component residues; and
R$^b$ is the same or different at each occurrence and represents one or more aromatic diamineresidues;
wherein 0.001-100 mol % of R$^a$ is a residue from one or more dianhydrides having Formula I.

All of the above-described embodiments for R$^a$ and R$^b$ in Formula II apply equally to R$^a$ and R$^b$ in Formula III.

Any of the above embodiments for Formula I in Formula III can be combined with one or more of the other embodiments, so long as they are not mutually exclusive.

In some embodiments, the polyimide has a repeat unit structure of Formula VI

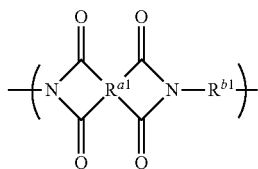

(VI)

where
R$^{a1}$ is the same or different at each occurrence and represents one or more tetracarboxylic acid component residues; and
R$^{b1}$ is the same or different at each occurrence and represents one or more aromatic diamineresidues;
wherein 0.001-100 mol % of R$^{b1}$ is a residue from one or more diamines having Formula IV.

All of the above-described embodiments for R$^{a1}$ and R$^{b1}$ in Formula V apply equally to R$^{a1}$ and R$^{b1}$ in Formula VI.

Any of the above embodiments for Formula IV in Formula VI can be combined with one or more of the other embodiments, so long as they are not mutually exclusive.

In some embodiments, the polyimide has a repeat unit structure of Formula IX

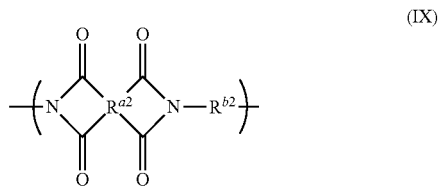

(IX)

where
R$^{a2}$ is the same or different at each occurrence and represents one or more tetracarboxylic acid component residues; and
R$^{b2}$ is the same or different at each occurrence and represents one or more aromatic diamineresidues;
wherein 0.001-100 mol % of R$^{b2}$ is a residue from one or more diamines having Formula VII.

All of the above-described embodiments for R$^{a2}$ and R$^{b2}$ in Formula VIII apply equally to R$^{a2}$ and R$^{b2}$ in Formula IX.

Any of the above embodiments for Formula VII in Formula IX can be combined with one or more of the other embodiments, so long as they are not mutually exclusive.

Polyimides can be made from any suitable polyimide precursor such as a polyamic acid, a polyamic acid ester, a polyisoimide, and a polyamic acid salt.

There is also provided a polyimide film, wherein the polyimide has a repeat unit structure of Formula III, Formula VI, or Formula IX, as described above.

Polyimide films can be made by coating a polyimide precursor onto a substrate and subsequently imidizing. This can be accomplished by a thermal conversion process or a chemical conversion process.

Further, if the polyimide is soluble in suitable coating solvents, it can be provided as an already-imidized polymer dissolved in the suitable coating solvent and coated as the polyimide.

In some embodiments, the polyimide film having repeat units of Formula III, Formula VI, or Formula IX has both a high glass transition temperature and a low optical retardation.

In some embodiments of the polyimide film, the glass transition temperature (T$_g$) is greater than 300° C. for a polyimide film cured at a temperature above 350° C.; in some embodiments, greater than 370° C.; in some embodiments, greater than 380° C.

In some embodiments of the polyimide film, the optical retardation is less than 120 at 550 nm; in some embodiments, less than 100; in some embodiments, less than 90.

In some embodiments of the polyimide film, the in-plane coefficient of thermal expansion (CTE) is less than 45 ppm/° C. between 50° C. and 200° C., for the first measurement; in some embodiments, less than 30 ppm/° C.; in some embodiments, less than 20 ppm/° C.; in some embodiments, less than 15 ppm/° C.

In some embodiments of the polyimide film, the in-plane coefficient of thermal expansion (CTE) is less than 75 ppm/° C. between 50° C. and 200° C., for the second measurement; in some embodiments, less than 65 ppm/° C.

In some embodiments of the polyimide film, the 1% TGA weight loss temperature is greater than 350° C.; in some embodiments, greater than 400° C.; in some embodiments, greater than 450° C.

In some embodiments of the polyimide film, the tensile modulus is between 1.5 GPa and 15.0 GPa; in some embodiments, between 1.5 GPa and 10.0 GPa; in some embodiments, between 1.5 and 7.5 GPa; in some embodiments, between 1.5 and 5.0 GPa.

In some embodiments of the polyimide film, the elongation to break is greater than 10%.

In some embodiments of the polyimide film, the haze is less than 1.0%; in some embodiments less than 0.5%.

In some embodiments of the polyimide film, the b* is less than 7.5; in some embodiments, less than 5.0.

In some embodiments of the polyimide film, the YI is less than 12; in some embodiments, less than 10.

In some embodiments of the polyimide film, the transmittance at 400 nm is greater than 40%; in some embodiments, greater than 50%.

In some embodiments of the polyimide film, the transmittance at 430 nm is greater than 60%; in some embodiments, greater than 70%.

In some embodiments of the polyimide film, the transmittance at 450 nm is greater than 70%; in some embodiments, greater than 80%.

In some embodiments of the polyimide film, the transmittance at 550 nm is greater than 70%; in some embodiments, greater than 80%.

In some embodiments of the polyimide film, the transmittance at 750 nm is greater than 70%; in some embodiments, greater than 80%.

Any of the above embodiments for the polyimide film can be combined with one or more of the other embodiments, so long as they are not mutually exclusive.

6. Methods for Preparing the Polyimide Films

Generally, polyimide films can be prepared from polyimide precursors by chemical or thermal conversion. In some embodiments, the films are prepared from the corresponding polyamic acid solutions by chemical or thermal conversion processes. The polyimide films disclosed herein, particularly when used as flexible replacements for glass in electronic devices, are prepared by thermal conversion processes.

Generally, polyimide films can be prepared from the corresponding polyamic acid solutions by chemical or thermal conversion processes. The polyimide films disclosed herein, particularly when used as flexible replacements for glass in electronic devices, are prepared by thermal conversion or modified-thermal conversion processes, versus chemical conversion processes.

Chemical conversion processes are described in U.S. Pat. Nos. 5,166,308 and 5,298,331 which are incorporated by reference in their entirety. In such processes, conversion chemicals are added to the polyamic acid solutions. The conversion chemicals found to be useful in the present invention include, but are not limited to, (i) one or more dehydrating agents, such as, aliphatic acid anhydrides (acetic anhydride, etc.) and acid anhydrides; and (ii) one or more catalysts, such as, aliphatic tertiary amines (triethylamine, etc.), tertiary amines (dimethylaniline, etc.) and heterocyclic tertiary amines (pyridine, picoline, isoquinoilne, etc.). The anhydride dehydrating material is typically used in a slight molar excess of the amount of amide acid groups present in the polyamic acid solution. The amount of acetic anhydride used is typically about 2.0-3.0 moles per equivalent of the polyamic acid. Generally, a comparable amount of tertiary amine catalyst is used.

Thermal conversion processes may or may not employ conversion chemicals (i.e., catalysts) to convert a polyamic acid casting solution to a polyimide. If conversion chemicals are used, the process may be considered a modified-thermal conversion process. In both types of thermal conversion processes, only heat energy is used to heat the film to both dry the film of solvent and to perform the imidization reaction. Thermal conversion processes with or without conversion catalysts are generally used to prepare the polyimide films disclosed herein.

Specific method parameters are pre-selected considering that it is not just the film composition that yields the properties of interest. Rather, the cure temperature and temperature-ramp profile also play important roles in the achievement of the most desirable properties for the intended uses disclosed herein. The polyamic acids should be imidized at a temperature at, or higher than, the highest temperature of any subsequent processing steps (e.g. deposition of inorganic or other layer(s) necessary to produce a functioning display), but at a temperature which is lower than the temperature at which significant thermal degradation/discoloration of the polyimide occurs. It should also be noted that an inert atmosphere is generally preferred, particularly when higher processing temperatures are employed for imidization.

For the polyamic acids/polyimides disclosed herein, temperatures of 300° C. to 320° C. are typically employed when subsequent processing temperatures in excess of 300° C. are required. Choosing the proper curing temperature allows a fully cured polyimide which achieves the best balance of thermal and mechanical properties. Because of this very high temperature, an inert atmosphere is required. Typically, oxygen levels in the oven of <100 ppm should be employed. Very low oxygen levels enable the highest curing temperatures to be used without significant degradation/discoloration of the polymer. Catalysts that accelerate the imidization process are effective at achieving higher levels of imidization at cure temperatures between about 200° C. and 300° C. This approach may be optionally employed if the flexible device is prepared with upper cure temperatures that are below the $T_g$ of the polyimide.

The amount of time in each potential cure step is also an important process consideration. Generally, the time used for the highest-temperature curing should be kept to a minimum. For 320° C. cure, for example, cure time can be up to an hour or so under an inert atmosphere, but at higher cure temperatures, this time should be shortened to avoid thermal degradation. Generally speaking, higher temperature dictates shorter time. Those skilled in the art will recognize the balance between temperature and time in order to optimize the properties of the polyimide for a particular end use.

In some embodiments, the polyamic acid solution is converted into a polyimide film via a thermal conversion process.

In some embodiments of the thermal conversion process, the polyamic acid solution is coated onto a matrix such that the soft-baked thickness of the resulting film is 10-50 μm.

In some embodiments of the thermal conversion process, the coated matrix is soft baked on a hot plate in proximity mode wherein nitrogen gas is used to hold the coated matrix just above the hot plate.

In some embodiments of the thermal conversion process, the coated matrix is soft baked on a hot plate in full-contact mode wherein the coated matrix is in direct contact with the hot plate surface.

In some embodiments of the thermal conversion process, the coated matrix is soft baked on a hot plate using a combination of proximity and full-contact modes.

In some embodiments of the thermal conversion process, the coated matrix is soft-baked using a hot plate set at 80-140° C.

In some embodiments of the thermal conversion process, the coated matrix is soft-baked for a total time of 2-10 minutes.

In some embodiments of the thermal conversion process, the soft-baked coated matrix is subsequently cured at 2-10 pre-selected temperatures for 2-10 pre-selected time intervals, the latter of which may be the same or different.

In some embodiments of the thermal conversion process, the pre-selected temperature is in the range of 80-450° C.

In some embodiments of the thermal conversion process, one or more of the pre-selected time intervals is 2 minutes.

In some embodiments of the thermal conversion process, one or more of the pre-selected time intervals is 5 minutes.

In some embodiments of the thermal conversion process, one or more of the pre-selected time intervals is 10 minutes.

In some embodiments of the thermal conversion process, one or more of the pre-selected time intervals is 15 minutes.

In some embodiments of the thermal conversion process, one or more of the pre-selected time intervals is greater than 15 minutes.

In some embodiments of the thermal conversion process, one or more of the pre-selected time intervals is between 2 minutes and 60 minutes.

In some embodiments of the thermal conversion process, one or more of the pre-selected time intervals is between 2 minutes and 120 minutes.

In some embodiments of the thermal conversion process, the method for preparing a polyimide film comprises the following steps in order: coatingthe above-described polyamic acid solution onto a matrix; soft-baking the coated matrix; treating the soft-baked coated matrix at a plurality of pre-selected temperatures for a plurality of pre-selected time intervals whereby the polyimide film exhibits properties that are satisfactory for use in electronics applications like those disclosed herein.

In some embodiments of the thermal conversion process, the method for preparing a polyimide film consists of the following steps in order: coatingthe above-described polyamic acid solution onto a matrix; soft-baking the coated matrix; treating the soft-baked coated matrix at a plurality of pre-selected temperatures for a plurality of pre-selected time intervals whereby the polyimide film exhibits properties that are satisfactory for use in electronics applications like those disclosed herein.

In some embodiments of the thermal conversion process, the method for preparing a polyimide film consists essentially of the following steps in order: coatingthe above-described polyamic acid solution onto a matrix; soft-baking the coated matrix; treating the soft-baked coated matrix at a plurality of pre-selected temperatures for a plurality of pre-selected time intervals whereby the polyimide film exhibits properties that are satisfactory for use in electronics applications like those disclosed herein.

Typically, the polyamic acid solutions/polyimides disclosed herein are coated/cured onto a supporting glass substrate to facilitate the processing through the rest of the display making process. At some point in the process as determined by the display maker, the polyimide coating is removed from the supporting glass substrate by a mechanical or laser lift off process. These processes separate the polyimide as a film with the deposited display layers from the glass and enable a flexible format. Often, this polyimide film with deposition layers is then bonded to a thicker, but still flexible, plastic film to provide support for subsequent fabrication of the display.

There are also provided modified-thermal conversion processes wherein conversion catalysts generally cause imidization reactions to run at lower temperatures than would be possible in the absence of such conversion catalysts.

In some embodiments, the polyamic acid solution is converted into a polyimide film via a modified-thermal conversion process.

In some embodiments of the modified-thermal conversion process, the polyamic acid solution further contains conversion catalysts.

In some embodiments of the modified-thermal conversion process, the polyamic acid solution further contains conversion catalysts selected from the group consisting of tertiary amines.

In some embodiments of the modified-thermal conversion process, the polyamic acid solution is coated onto the matrix such that the soft-baked thickness of the resulting film is less than 10-50 μm.

In some embodiments of the modified-thermal conversion process, the coated matrix is soft baked on a hot plate in proximity mode wherein nitrogen gas is used to hold the coated matrix just above the hot plate.

In some embodiments of the modified-thermal conversion process, the coated matrix is soft baked on a hot plate in full-contact mode wherein the coated matrix is in direct contact with the hot plate surface.

In some embodiments of the modified-thermal conversion process, the coated matrix is soft baked on a hot plate using a combination of proximity and full-contact modes.

In some embodiments of the modified-thermal conversion process, the coated matrix is soft-baked using a hot plate set at 80-150° C.

In some embodiments of the modified-thermal conversion process, the coated matrix is soft-baked for a total time of 2-10 minutes.

In some embodiments of the modified-thermal conversion process, the soft-baked coatedmatrix is subsequently cured at 2-10 pre-selected temperatures for 2-10 pre-selected time intervals, the latter of which may be the same or different.

In some embodiments of the modified-thermal conversion process, the pre-selected temperature is greater than 80-300° C.

In some embodiments of the modified-thermal conversion process, one or more of the pre-selected time intervals is between 2 minutes and 120 minutes.

In some embodiments of the modified-thermal conversion process, the method for preparing a polyimide film comprises the following steps in order: coatingthe above-described polyamic acid solution including a conversion chemical onto a matrix; soft-baking the coated matrix; treating the soft-baked coated matrix at a plurality of pre-selected temperatures for a plurality of pre-selected time intervals whereby the polyimide film exhibits properties that are satisfactory for use in electronics applications like those disclosed herein.

In some embodiments of the modified-thermal conversion process, the method for preparing a polyimide film consists of the following steps in order: coatingthe above-described polyamic acid solution including a conversion chemical onto a matrix; soft-baking the coated matrix; treating the soft-baked coated matrix at a plurality of pre-selected temperatures for a plurality of pre-selected time intervals whereby the polyimide film exhibits properties that are satisfactory for use in electronics applications like those disclosed herein.

In some embodiments of the modified-thermal conversion process, the method for preparing a polyimide film consists essentially of the following steps in order: coatingthe above-described polyamic acid solution including a conversion chemical onto a matrix; soft-baking the coated matrix; treating the soft-baked coated matrix at a plurality of pre-selected temperatures for a plurality of pre-selected time intervals whereby the polyimide film exhibits properties that are satisfactory for use in electronics applications like those disclosed herein.

7. The Electronic Device

The polyimide films disclosed herein can be suitable for use in a number of layers in electronic display devices such as OLED and LCD Displays. Nonlimiting examples of such layers include device substrates, touch panels, substrates for color filter sheets, cover films, and others. The particular materials' properties requirements for each application are unique and may be addressed by appropriate composition(s) and processing condition(s) for the polyimide films disclosed herein.

In some embodiments, the flexible replacement for glass in an electronic device is a polyimide film having the repeat unit of Formula III, Formula VI, or Formula IX, as described in detail above.

Organic electronic devices that may benefit from having one or more layers including at least one compound as described herein include, but are not limited to, (1) devices that convert electrical energy into radiation (e.g., a light-emitting diode, light emitting diode display, lighting device, luminaire, or diode laser), (2) devices that detect signals through electronics processes (e.g., photodetectors, photo-conductive cells, photoresistors, photoswitches, phototransistors, phototubes, IR detectors, biosensors), (3) devices that convert radiation into electrical energy, (e.g., a photovoltaic device or solar cell), (4) devices that convert light of one wavelength to light of a longer wavelength, (e.g., a down-converting phosphor device); and (5) devices that include one or more electronic components that include one or more organic semi-conductor layers (e.g., a transistor or diode). Other uses for the compositions according to the present invention include coating materials for memory storage devices, antistatic films, biosensors, electrochromic devices, solid electrolyte capacitors, energy storage devices such as a rechargeable battery, and electromagnetic shielding applications.

Figure 2:
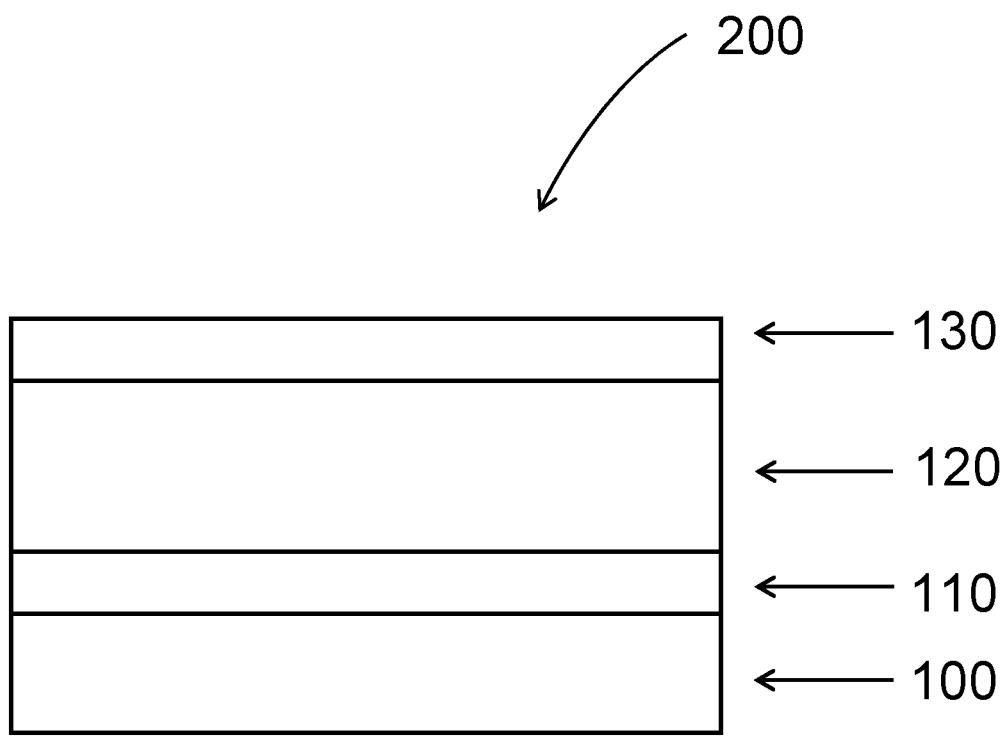
FIG. 2 includes an illustration of one example of an electronic device that includes a flexible replacement for glass.

One illustration of a polyimide film that can act as a flexible replacement for glass as described herein is shown in FIG. 1. The flexible film 100 can havethe properties as described in the embodiments of this disclosure. In some embodiments, the polyimide film that can act as a flexible replacement for glass is included in an electronic device. FIG. 2 illustrates the case when the electronic device 200 is an organic electronic device. The device 200 has a substrate 100, an anode layer 110 and a second electrical contact layer, a cathode layer 130, and a photoactive layer 120 between them. Additional layers may optionally be present. Adjacent to the anode may be a hole injection layer (not shown), sometimes referred to as a buffer layer. Adjacent to the hole injection layer may be a hole transport layer (not shown), including hole transport material. Adjacent to the cathode may be an electron transport layer (not shown), including an electron transport material. As an option, devices may use one or more additional hole injection or hole transport layers (not shown) next to the anode 110 and/or one or more additional electron injection or electron transport layers (not shown) next to the cathode 130. Layers between 110 and 130 are individually and collectively referred to as the organic active layers. Additional layers that may or may not be present include color filters, touch panels, and/or cover sheets. One or more of these layers, in addition to the substrate 100, may also be made from the polyimide films disclosed herein.

The different layers will be discussed further herein with reference to FIG. 2. However, the discussion applies to other configurations as well.

In some embodiments, the different layers have the following range of thicknesses: substrate 100, 5-100 microns, anode 110, 500-5000 Å, in some embodiments, 1000-2000 Å; hole injection layer (not shown), 50-2000 Å, in some embodiments, 200-1000 Å; hole transport layer (not shown), 50-3000 Å, in some embodiments, 200-2000 Å; photoactive layer 120, 10-2000 Å, in some embodiments, 100-1000 Å; electron transport layer (not shown), 50-2000 Å, in some embodiments, 100-1000 Å; cathode 130, 200-10000 Å, in some embodiments, 300-5000 Å. The desired ratio of layer thicknesses will depend on the exact nature of the materials used.

In some embodiments, the organic electronic device (OLED) contains a flexible replacement for glass as disclosed herein.

In some embodiments, an organic electronic device includes a substrate, an anode, a cathode, and a photoactive layer therebetween, and further includes one or more additional organic active layers. In some embodiments, the additional organic active layer is a hole transport layer. In some embodiments, the additional organic active layer is an electron transport layer. In some embodiments, the additional organic layers are both hole transport and electron transport layers.

In some embodiments, the device has the following structure, in order: substrate, anode, hole injection layer, hole transport layer, photoactive layer, electron transport layer, electron injection layer, cathode.

Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety.

EXAMPLES

The concepts described herein will be further illustrated in the following examples, which do not limit the scope of the invention described in the claims.

Synthesis Example 1

This example illustrates the preparation of a diamine having Formula IV, Compound IV-3.

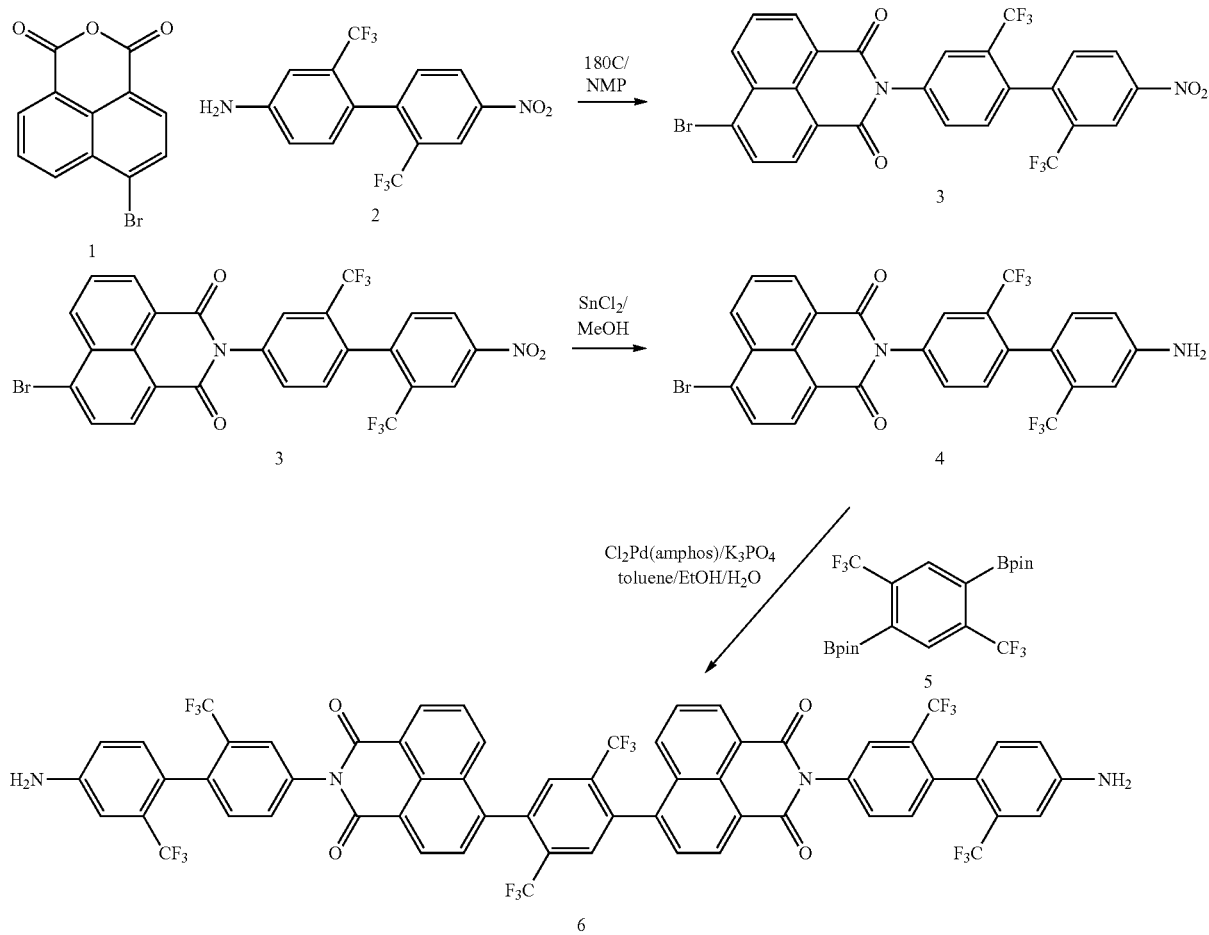

4-Bromo-N-(2,2'-bis(trifluoromethyl)-4'-amino-1,1'-biphenyl-4-yl)naphthalimide (3)

4-Bromo-1,8-naphthalenedicarboxylic anhydride 1 (25 g, 90.23 mmole), 4'-nitro-2,2'-bis(trifluoromethyl)-[1,1'-biphenyl]-4-amine 2 (31.7 g, 90.5 mmole), stirred with NMP (100 ml) at 180° C. under nitrogen atmosphere for 5 hours. Reaction mixture cooled down, diluted with water, precipitate collected by filtration, washed with water, dried. Solids dissolved in 1 L of hot chloroform, passed through a short column filled with silica gel eluating with chloroform. Chloroform distilled off using rotary evaporator to minimal volume followed by addition of methanol. Precipitate collected by filtration, dried to give 4-bromo-N-(2,2'-bis(trifluoromethyl)-4'-amino-1,1'-biphenyl-4-yl)naphthalimide3 (total yield—36.43 g). MS: MH+=609. $^1$H NMR (CDCl$_3$): 7.48 (d, 1H, J=9 Hz), 7.61 (dd, 1H, J1=8 Hz, J2=2 Hz), 7.66 (d, 1H, J=9 Hz), 7.79 (d, 1H, J=2 Hz), 7.95 (dd, 1H, J1=8 Hz, J2=7.5 Hz), 8.14 (d, 1H, J=7.5 Hz), 8.48 (dd, 1H, J1=9 Hz, J2=2 Hz), 8.51 (d, 1H, J=8 Hz), 8.69 (d, 1H, J=2 Hz), 8.71 (dd, 1H, J1=9 Hz, J2=1 Hz), 8.75 (dd, 1H, J1=7 Hz, J2=1 Hz).

4-Amino-N-(2,2'-bis(trifluoromethyl)-4'-amino-1,1'-biphenyl-4-yl)naphthalimide (4)

A mixture of 4-bromo-N-(2,2'-bis(trifluoromethyl)-4'-amino-1,1'-biphenyl-4-yl)naphthalimide3 (29 g, 47.6 mmole), tin chloride dihydrate (42.95 g, 190 mmole) in methanol (150 ml) was stirred at reflux for 4 hour. Reaction mixture cooled down, diluted with water (100 ml), crude product collected by filtration, washed with a mixture of methanol: water (1:1). Crude product dissolved in acetonitrile, passed through a filter filled with silica gel and basic alumina eluating with acetonitrile. Acetontirile distilled to minimal amount to give compound 4 that was used for the next step without further purification. 5.72 (s, 2H), 6.82 (dd, 1H, J1=9 Hz, J2=2 Hz), 6.99 (d, 1H, J=2 Hz), 7.03 (d, 1H, J=9 Hz), 7.45 (d, 1H, J=8 Hz), 7.69 (dd, 1H, J1=8 Hz, J2=2 Hz), 7.91 (d, 1H, J=2 Hz), 8.06 (dd, 1H, J1=8 Hz, J2=7.5 Hz), 8.29 (d, 1H, J=8 Hz), 8.37 (d, 1H, J=8 Hz), 8.61 (d, 1H, J=7 Hz), 8.64 (dd, 1H, J1=9 Hz, J2=1 Hz).

6,6'-[2,5-Bis(trifluoromethyl)-1,4-phenylene]bis[2-(2,2'-bis(trifluoromethyl)-4'-amino-1,1'-biphenyl-4-yl)-1H-benz[de]isoquinoline-1,3(2H)-dione (6), Compound IV-3

A mixture of 4-amino-N-(2,2'-bis(trifluoromethyl)-4'-amino-1,1'-biphenyl-4-yl)naphthalimide4 (7.82 g, 13.5 mmole), 2,2'-[2,5-bis(trifluoromethyl)-1,4-phenylene]bis[4,4,5,5-tetramethyl-1,3,2-dioxaborolane 5 (3.15 g, 6.75 mmole), Cl$_2$Pd(amphos) (0.143 g, 0.2025 mmole), potassium phosphate (7.16 g, 33.75 mmole) in toluene (100 ml), ethanol (40 ml), water (20 ml) was stirred at 100° C. for 1 hour. Reaction mixture cooled down, product filtered, washed with toluene and water, dried to give 7.48 g of crude product with purity apporx. 95% by UPLC. Crude product dissolved in tetrahydrofuran, passed through a filter fileld with silica gel, florisil and basic alumina eluating with tetrahydrofuran. The residue after evaporation of tetrahydrofuran was repeatatively crystallized from tetrahydrofuran-hexanes mixture to afford product with purity greater than 99.5%. $^1$H-NMR (dmso-d6): 5.74 (s, 4H), 6.85 (d, 2H, J=8 Hz), 7.02 (d, 2H, J=2 Hz), 7.07 (d, 2H, J=8 Hz), 7.95-8.07 (m, 6H), 8.17 (s, 2H), 8.63 (t, 2H, J=8 Hz), 8.66 (d, 1H, J=8 Hz), 8.70 (d, 1H, J=7 Hz).

Synthesis Example 2

This example illustrates the preparation of a dianhydride having Formula I, 6,6'-[2,5-bis(trifluoromethyl)-1,4-phenylene]bis-1H,3H-naphtho[1,8-cd]pyran-1,3-dione (7), Compound 1-2.

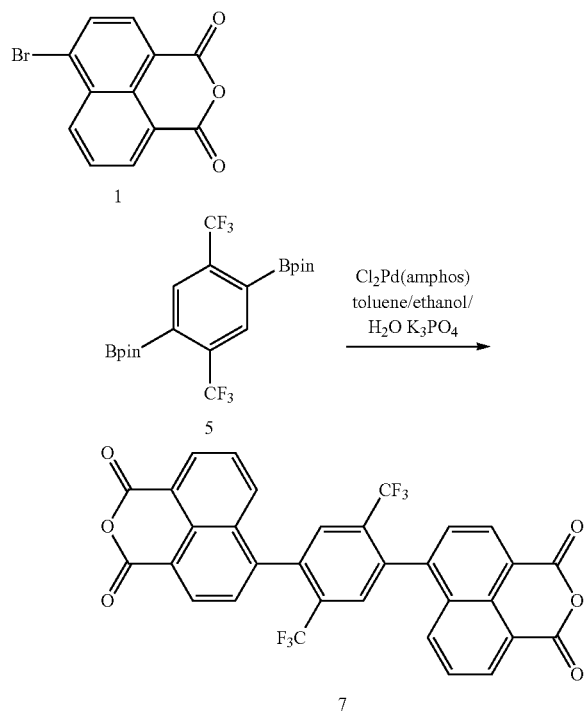

A mixture of 4-bromo-1,8-naphthalenedicarboxylic anhydride 1 (1.249 g, 4.51 mmole), 2,2'-[2,5-bis(trifluoromethyl)-1,4-phenylene]bis[4,4,5,5-tetramethyl-1,3,2-dioxaborolane 5 (1 g, 2.15 mmole), Cl$_2$Pd(amphos) (0.046 g, 0.0645 mmole), potassium phosphate (2.281 g, 10.75 mmole) in toluene (50 ml), ethanol (20 ml), water (10 ml) was stirred at 100° C. for 3 hours. Reaction mixture decanted hot, precipitate ashed with water, acetone, stirred in water (30 ml) with addition of concentrated hydrochloric acid for 2 hours, filtered, dried to give 1.24 g of crude product. Crude product was treated with 30 ml of dimethylsulfoxide, filtered, precipitate washed with water to give desired product with purity 99.51% by HPLC. Filtrate was diluted with water (100 ml), precipitate collected by filtration, stirred with acetic anhydride (10 ml) at 140 C for 2 hours, precipitate collected by filtration to give desired product with purity 99.1%. MS: MH+=607. $^1$H-NMR (dmso-d6): 7.92-8.04 (m) and 8.29 (d, J=8.8 Hz) atropoisomers (6H), 8.12 (s, 2H), 8.61-8.71 (m, 4H, atropoisomers). Photoluminescence: λ=418±5 nm in tetrahydrofuran, quantum yield—59%.

Polymer Example 1

This example illustrates the preparation of a polyamic acid using diamine Compound IV-3.

A mixture of Compound IV-3 from Synthesis Example 1 (3.733 g), 3,3',4,4'-biphenyltetracarboxylic dianhydride (0.889 g) and N-methylpyrrolidinone (27 g) was stirred in glass reactor at ambient temperature followed by addition of pyromellitic dianhydride (8 mg) until final viscosity 13670 cP. GPC: Mn=75827, Mw=163321, Mp=150475, Mz=272075, PDI=2.15.

Polymer Example 2

This example illustrates the preparation of a polyamic acid using diamine Compound IV-3.

A mixture of Compound IV-3 from Synthesis Example 1 (4.919 g), 3,3',4,4'-biphenyltetracarboxylic dianhydride (1.171 g), 5,5'-[2,2,2-trifluoro-1-(trifluoromethyl)ethylidene]bis-1,3-isobenzofurandione 6FDA (36 mg) and N-methylpyrrolidinone (41 g) was stirred in glass reactor at ambient temperature followed by addition of 6FDA (36 mg) in two portions until final viscosity 1565 cP.

Film Example 1

This example illustrates the preparation of a polyimide film.

The polyamic acid solution from Polymer Example 1 was filtered through microfilter, spun coated onto clean silicon wafers, soft-baked at 90° C. on hotplate, placed into a furnace. The furnace was heated to a maximum cure temperature 375° C. under nitrogen atmosphere, in stages. Wafers were removed from furnace, soaked in water and manually delaminated to yield samples of polyimide film with thickness 11.6 μm.

A Hunter Lab spectrophotometer was used to measure b* and yellow index along with % transmittance (% T) over the wavelength range 350 nm-780 nm. Thermal measurements on films were made using a combination of thermogravimetric analysis and thermomechanical analysis as appropriate for the specific parameters reported herein. Mechanical properties were measured using equipment from Instron.

The film properties are given below:
Thickness=11.6 μm
Tg>450° C.
CTE=2.66 ppm/° C.
Haze=1.27%
b*=14.4
YI=22.5
η=0.1018 birefringence Film Example 2

This example illustrates the preparation of a polyimide film.

The polyamic acid solution from Polymer Example 2 was filtered through microfilter, spun coated onto clean silicon wafers, soft-baked at 90° C. on hotplate, placed into a furnace. The furnace was heated to a maximum cure temperature 375° C. under nitrogen atmosphere, in stages. Wafers were removed from furnace, soaked in water and manually delaminated to yield samples of polyimide film with thickness 10.26 μm.

A Hunter Lab spectrophotometer was used to measure b* and yellow index along with % transmittance (% T) over the wavelength range 350 nm-780 nm. Thermal measurements on films were made using a combination of thermogravimetric analysis and thermomechanical analysis as appropriate for the specific parameters reported herein. Mechanical properties were measured using equipment from Instron.

The film properties are given below:

Thickness=10.26 μm

Tg=495° C.

CTE=6.2 ppm/° C.

Haze=0.5% b*=7.32

YI=12.85

η=0.0954 birefringence

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. The use of numerical values in the various ranges specified herein is stated as approximations as though the minimum and maximum values within the stated ranges were both being preceded by the word "about." In this manner, slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:

1. A dianhydride having Formula I

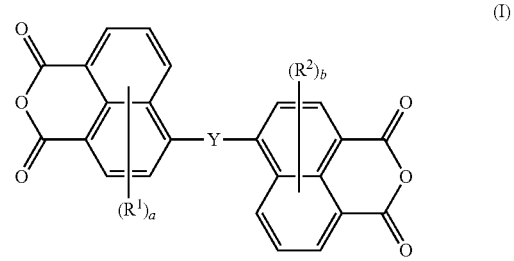

wherein:
Y is selected from the group consisting of alkyl, silyl, ester, siloxane, oligosiloxane, polysiloxane, $SO_2$, $BR^3$, $NR^3$, $P(O)R^3$, unsubstituted or substituted carbocyclic aryl, and unsubstituted or substituted heteroaryl and deuterated analogs thereof;
$R^1$-$R^2$ are the same or different at each occurrence and are selected from the group consisting of F, CN, deuterium, alkyl, fluoroalkyl, unsubstituted or substituted carbocyclic aryl, unsubstituted or substituted heteroaryl, alkoxy, fluoroalkoxy, unsubstituted or substituted aryloxy, silyl, and siloxy and deuterated analogs thereof;
$R^3$ is selected from the group consisting of alkyl and unsubstituted or substituted carbocyclic aryl and deuterated analogs thereof; and
a and b are the same or different and are an integer from 0-5.

2. A diamine having Formula IV or Formula VII

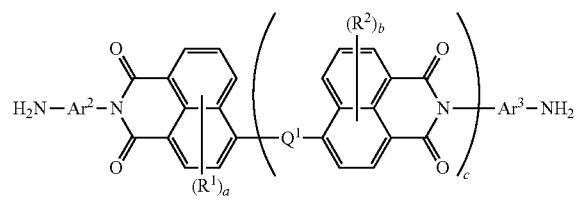

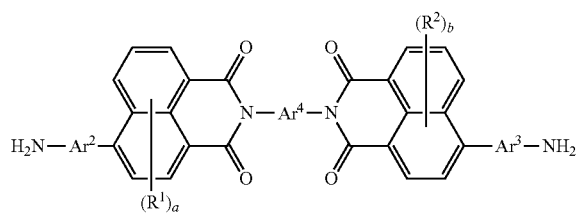

wherein:
$Ar^2$, $Ar^3$, and $Ar^4$ are the same or different and are selected from the group consisting of carbocyclic aryl, heteroaryl, and substituted derivatives thereof and deuterated analogs thereof;
$Q^1$ is selected from the group consisting of a single bond, alkyl, silyl, ester, siloxane, oligosiloxane, polysiloxane, O, S, $SO_2$, $BR^3$, $NR^3$, $P(O)R^3$, unsubstituted or substituted carbocyclic aryl, and unsubstituted or substituted heteroaryl and deuterated analogs thereof;

R¹ and R² are the same or different at each occurrence and are selected from the group consisting of F, CN, deuterium, alkyl, fluoroalkyl, unsubstituted or substituted carbocyclic aryl, unsubstituted or substituted heteroaryl, alkoxy, fluoroalkoxy, unsubstituted or substituted aryloxy, silyl, siloxy and deuterated analogs thereof;

R³ is selected from the group consisting of alkyl and unsubstituted or substituted carbocyclic aryl and deuterated analogs thereof; and a and b are the same or different and are an integer from 0-5; and c is 0 or 1.

3. A polyamic acid having a repeat unit structure of Formula II

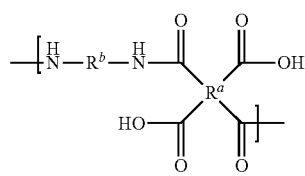

(II)

where:
R$^a$ is the same or different at each occurrence and represents one or more tetracarboxylic acid component residues; and R$^b$ is the same or different at each occurrence and represents one or more aromatic diamine residues;

wherein 0.001-100 mol % of R$^a$ is a residue from one or more dianhydrides having Formula I according to claim 1.

4. A polyamic acid having a repeat unit structure of Formula V or Formula VIII

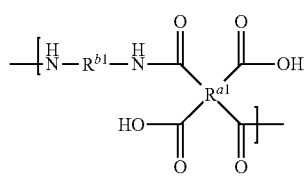

(V)

(VIII)

where:
R$^{a1}$ is the same or different at each occurrence and represents one or more tetracarboxylic acid component residues; and R$^{a2}$ is the same or different at each occurrence and represents one or more tetracarboxylic acid component residues;

R$^{b1}$ is the same or different at each occurrence and represents one or more aromatic diamine residues; and R$^{b2}$ is the same or different at each occurrence and represents one or more aromatic diamine residues;

wherein 0.001-100 mol % of R$^{b1}$ is a diamine residue from one or more diamines having Formula IV according to claim 2; and wherein 0.001-100 mol % of R$^{b2}$ is a diamine residue from one or more diamines having Formula VII according to claim 2.

5. A polyimide having a repeat unit structure of Formula III

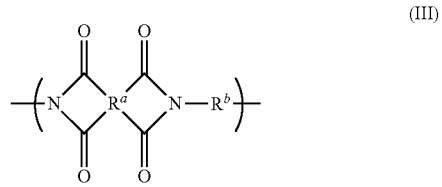

(III)

where
R$^a$ is the same or different at each occurrence and represents one or more tetracarboxylic acid component residues; and R$^b$ is the same or different at each occurrence and represents one or more aromatic diamine residues;

wherein 0.001-100 mol % of R$^a$ is a residue from one or more dianhydrides having Formula I according to claim 1.

6. A polyimide having a repeat unit structure of Formula VI or Formula IX

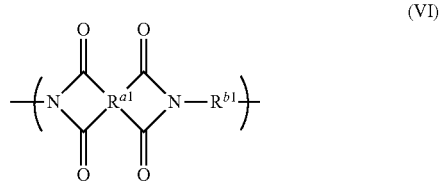

(VI)

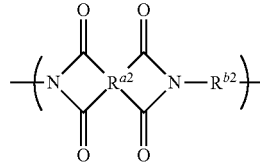

(IX)

where:
R$^{a1}$ is the same or different at each occurrence and represents one or more tetracarboxylic acid component residues; and R$^{a2}$ is the same or different at each occurrence and represents one or more tetracarboxylic acid component residues;

R$^{b1}$ is the same or different at each occurrence and represents one or more aromatic diamine residues; and R$^{b2}$ is the same or different at each occurrence and represents one or more aromatic diamine residues;

wherein 0.001-100 mol % of R$^{b1}$ is a diamine residue from one or more diamines having Formula IV according to claim 2; and wherein 0.001-100 mol % of R$^{b2}$ is a diamine residue from one or more diamines having Formula VII according to claim 2.

7. A flexible replacement for glass in an electronic device wherein the flexible replacement for glass comprises a polyimide film having a repeat unit of Formula III, according to claim 5.

8. An electronic device comprising the flexible replacement for glass, according to claim 7.

9. A flexible replacement for glass in an electronic device wherein the flexible replacement for glass comprises a polyimide film having a repeat unit of Formula IV or Formula IX, according to claim 6.

10. An electronic device comprising the flexible replacement for glass, according to claim 9.

* * * * *